(12) United States Patent
Yang et al.

(10) Patent No.: US 8,586,369 B2
(45) Date of Patent: Nov. 19, 2013

(54) ION CHANNEL-FORMING PEPTIDES

(75) Inventors: Jerry Yang, La Jolla, CA (US); Steven Blake, La Jolla, CA (US); Michael Mayer, Ann Arbor, MI (US)

(73) Assignee: The Regents of the University of California, Oakland, CA (US)

( * ) Notice: Subject to any disclaimer, the term of this patent is extended or adjusted under 35 U.S.C. 154(b) by 394 days.

(21) Appl. No.: 12/668,178

(22) PCT Filed: Jul. 9, 2008

(86) PCT No.: PCT/US2008/069554
§ 371 (c)(1),
(2), (4) Date: Nov. 12, 2010

(87) PCT Pub. No.: WO2009/009613
PCT Pub. Date: Jan. 15, 2009

(65) Prior Publication Data
US 2011/0046020 A1    Feb. 24, 2011

Related U.S. Application Data

(60) Provisional application No. 60/948,689, filed on Jul. 9, 2007.

(51) Int. Cl.
*G01N 33/00*    (2006.01)

(52) U.S. Cl.
USPC .............. 436/86; 436/15; 436/149; 435/4

(58) Field of Classification Search
USPC ............................ 436/15, 86, 149; 435/4
See application file for complete search history.

(56) References Cited

U.S. PATENT DOCUMENTS 5,874,316 A * 2/1999 Cornell et al. ............ 436/518

* cited by examiner

*Primary Examiner* — Monique Cole
(74) *Attorney, Agent, or Firm* — Kilpatrick Townsend & Stockton LLP

(57) ABSTRACT

The invention pertains generally to novel compositions and methods for constructing chemically sensitive ion channels. The compositions and methods include, for example, novel gramicidin A derivatives and their use in constructing novel ion channels for use as biosensors.

17 Claims, 17 Drawing Sheets formyl-HN-L-Val-Gly-L-Ala-D-Leu-L-Ala-D-Val-L-Val-D-Val-L-Trp-D-Leu-L-Trp-D-Leu-L-Trp-D-Leu-L-Trp-CO-X

Other reagents (commercial): Biotin-NHS

X = HCO-Val-Gly-Ala-Leu-Ala-Val-Val-Val-Trp-Leu-Trp-Leu-Trp-Leu-Trp—

1 = gramicidin A
2 = gramicidamine
3 = gramicidazide
4 = 2-aminoethyl gramicidate
5 = desethanolamine gramicidin A X = HCO-Val-Gly-Ala-Leu-Ala-Val-Val-Val-Trp-Leu-Trp-Leu-Trp-Leu-Trp—

US 8,586,369 B2

ION CHANNEL-FORMING PEPTIDES

CROSS REFERENCE TO RELATED APPLICATIONS

This application claims priority to U.S. Provisional Application Ser. No. 60/948,689 filed Jul. 9, 2007, the disclosure of which is incorporated herein by reference in its entirety for all purposes.

STATEMENT REGARDING FEDERALLY SPONSORED RESEARCH

The contents of this application were made with Government support under Grant Number NIAID 5 P30 AI36214. The Government has certain rights in the invention(s) provided herein.

TECHNICAL FIELD

The present application pertains generally to novel compositions and methods for constructing chemically sensitive ion channels.

BACKGROUND

The detection of chemical processes on a single molecule scale is the ultimate goal of sensitive analytical assays. Derivatives of gramicidin A (gA) show promise as ultrasensitive transducers for detecting chemical and biochemical analytes due to the high amplification that is inherent to the ion channel activity of these helical peptides. In general, the opening of a single ion channel results in the measurable flux of about 103 to 106 ions per millisecond across lipid membranes. Gramicidin A is a natural ion channel-forming peptide secreted by the bacterium *Bacillus brevis*. The peptide facilitates a transmembrane flux of monovalent cations upon reversible head-to-head dimerization in lipid bilayers. Gramicidin A is well suited for biosensor applications due to its defined and quantized characteristics of ion channel conductance. For example, the majority of ion channel proteins are reconstituted into bilayers by proteoliposome fusion. In contrast, gA can be dissolved in aqueous solutions and spontaneously incorporates into bilayers. Once in the membrane, gA self-assembles into a functional dimeric nanostructure with characteristic, transient ion flux.

The C-terminus of gA may be derivatized chemically without loss of ion channel activity. Changes in the single-channel conductance, γ, of gA in response to derivatization at the C-terminus may be detected. In general there is low background interference of the ion channel signal detected from non-ionic molecules in solution. For example, an ion channel-based sensor does not rely on optical detection. Accordingly, colored molecules in solution do not interfere provided that they do not influence the passage of monovalent cations through gA pores or alter significantly the ionic strength of the recording buffer. With regards to interference, several characteristics of gA pores are important to consider. for example, only small monovalent cations (e.g., monovalent metal ions or protons) can pass through gA channels. Divalent cations such as Ca2+ are known to block gA channels at concentrations≥100 mM (see Bamberg and Lauger, Membrane Biol., 1977, 35, 351-375). Large concentrations of monovalent cations or divalent cations from analytical samples can therefore be expected to cause interference. Molecules larger than 5 Å cannot pass since gA channels have a diameter of ~4 Å; these large molecules are not expected to cause significant interference (regardless of whether they are colored or fluorescent) as long as they cannot block gA pores. Therefore, the presence of significant concentrations of monovalent or divalent cations should be accounted for when measuring the conductance of gA derivatives (for instance by calibration or standard addition).

In order to exploit the potentially useful advantages of gA for detection purposes, several groups have explored the use of gA for a number of sensor applications. One of the first descriptions of sensor based on gramicidin A was in 1997 (Cornell et al., Nature 1997, 387, 580-583). Other ion channel platforms such as ion channel proteins (e.g., a-Hemolysin: Bayley and Cremer, Nature 2001, 413, 226-230; Luchian et al., Chem., Int. Ed. 2003, 42, 3766-3771; Luchian et al., Chem., Int. Ed. 2003, 42, 1925-1929; Shin et al., Chem., Int. Ed. 2002, 41, 3707-3709) have provided further demonstrations of the potential advantages of using ion channels as sensors.

The proteins used in previous studies often require genetic engineering and molecular biology expertise and are less amenable to a large user base. Derivatives of gA, for instance, have been used to sense protein-ligand interactions (Cornell et al., Nature 1997, 387, 580-583), redox potential of the electrolyte solution (Antonenko et al., Biochim. Biophys. Acta 2006, 1758, 493-498.) ammonium ions (Nikolelis and Siontorou, Anal. Chem. 1996, 68, 1735-1741.), light (Stankovic et al., Biochim. Biophys. Acta 1991, 1061, 163-170; Banghart eta al., Biochemistry 2006, 45, 15129-15141.) and pH at membrane interfaces (Borisenko et al., Biochim. Biophys. Acta 2002, 1558, 26-33).

Others have demonstrated that charged derivatives of gA can have markedly different conductance values based on the polarity and number of the attached charges (Bamberg et al., Proc. Natl. Acad. Sci. USA, 1978, 37, 2633-2638; Apell et al., Biochim. Biophys. Acta 1979, 552, 369-378). In addition, the functional properties of a chemical analyte (i.e. its reactivity with certain functional groups) can be used to change the chemical properties (i.e., the charge) of these reactive groups covalently attached to the opening of gA. This change in chemical properties can be monitored in situ by using single ion channel recordings (see e.g., FIG. 1; see also Blake et al., Chembiochem 2006, 7, 433-435, 34).

Among the largest limitations of using ion channel-forming peptides such as gramicidin A for development of sensors is the synthetic accessibility of the peptide for readily generating tailored ion channels. Previously described chemical methods for synthesizing C-terminal derivatives of gramicidin A generally include procedures such as esterification (Blake et al., Chembiochem. 2006, 7, 433-435; Apell et al., Membr. Biol. 1977, 31, 171-188; Futaki et al., Bioorg. Med. Chem. 2004, 12, 1343-1350), carbamoylation (Borisenko et al., Biochim. Biophys. Acta 2002, 1558, 26-33), or solid phase synthesis (Roeske et al., Biochim. Biophys. Acta 1989, 982, 223-227). Such procedural limitations represent potential bottlenecks in the development of gramicidin A-based ion channel sensors.

There is a need for derivatives of gA that may be useful as a platform for sensing chemical or biochemical analytes that change the charge of functional groups attached to the entrance of these semi-synthetic nanopores.

SUMMARY

Provided herein are novel gramicidin A derivatives for synthesizing stable ion channel sensors, methods of using these derivatives for synthesizing ion channel sensors, and methods of using these derivatives as synthetic intermediates for generating tailored gramicidin. A-based sensors. Gramicidin A derivatives provided herein represent highly synthetically reactive intermediates that can be used to efficiently synthesize ion channel sensors.

In one embodiment, an isolated ionophore conjugate is provided. The conjugate includes an ion channel forming peptide and a substrate associated with the peptide. In general the charge of the substrate is modifiable by a target analyte. A change in the charge of the substrate detectably alters the flow of ions associated with the ionophore.

In some aspects the substrate is associated with the peptide at the entrance (i.e., pore) of a channel formed by the peptide.

In some aspects the ion channel forming peptide is selected from the group consisting of gramicidin, band three protein, bacteriorhodopsin, proteorhodopsin, mellitin, alamethicin, an alamethicin analogue, porin, tyrocidine, tyrothricin, and valinomycin. The gramicidin may be gramicidin A, gramicidin B, gramicidin C, gramicidin D, gramicidin GT, gramicidin GM, gramicidin GM−, gramicidin GN−, or gramicidin A'.

In some aspects, the target analyte is an enzyme such as a phosphatase or a kinase.

In other aspects, the substrate comprises a moiety suitable for phosphorylation. In another aspect, the substrate comprises a moiety suitable for de-phosphorylation by a phosphatase such as alkaline phosphatase. The moiety may be a negatively-charged phosphate group.

In one aspect, the substrate is glycolic-O-phosphate.

In some embodiments the ionophore conjugate further includes a spacer group that covalently links the ionophore to the substrate moiety. In some aspects, the spacer group is selected from the group consisting alkyl, alkyl amides, alkyl esters, alkyl carbamates, alkyl carbonates, oligomers of alkylidene glycol, combinations of oligomers of ethylene glycol with amides, esters or carbamates, and oligopeptides.

In one aspect the analyte is derived from a biological fluid.

In another embodiment, a membrane is provided. The membrane includes a first and a second layer each comprising closely packed amphiphilic molecules; and a plurality of ionophore conjugates comprising an ion channel forming peptide and a substrate associated with the peptide. The charge of the substrate is modifiable by a target analyte. A change in the charge of the substrate detectably alters the flow of ions associated with the ionophore. The flow of ions across the membrane via the ionophore conjugates may be increased or decreased.

In some aspects the amphiphilic molecules are phospholipids that are zwitterionic or charged differently than the ion channel forming peptide.

In another embodiment, a biosensor that includes a membrane described herein is provided. The biosensor includes a solid conducting surface anchoring the membrane in a manner such that a reservoir exists between the membrane and the solid conducting surface. In some aspects, the biosensor further includes a recording buffer having a low pH that supports maintenance of a detectable flow of ions.

In another embodiment, a device that includes an array of biosensors is provided.

In yet another embodiment, a method for detecting a target analyte in a biological sample is provided. the method includes contacting a biosensor provided herein with a biological sample and detecting a change in the conductance of the ionophore conjugates associated with the biosensor. In general, a change in conductance is indicative of the presence of a target analyte.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

Like reference symbols in the various drawings indicate like elements.

DETAILED DESCRIPTION

Figure 1:
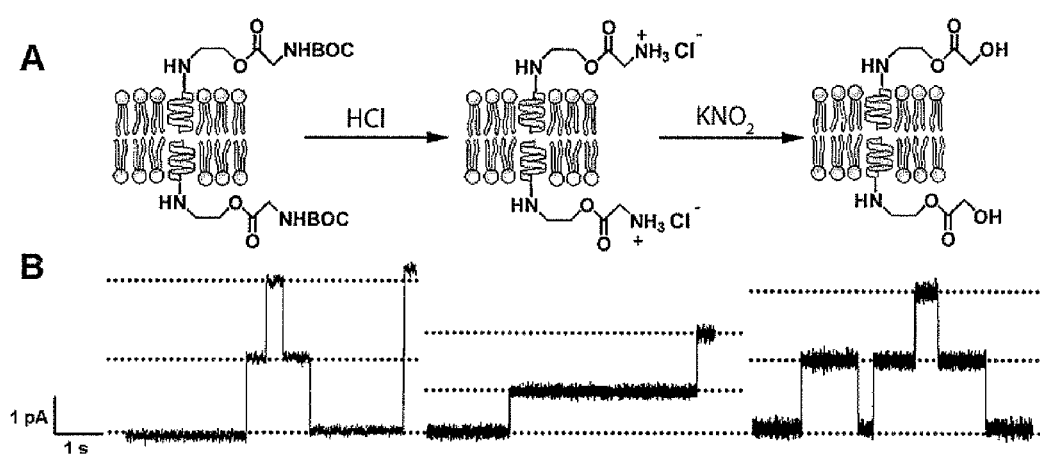
FIG. 1 depicts monitoring transformations of chemical groups on molecules attached to the C-terminus of gramicidin A (gA) by measurement of single ion channel currents. A) Cartoon of a two-step conversion of gA carrying a tert-butyloxycarbonyl-protected (BOC-protected) glycine group (left) to gA carrying a glycolic acid group in the presence of externally added reagents in solution. B) Representative single ion channel traces of the corresponding derivatives of gA shown in part A (for comparison, all three derivatives were recorded in 1.00 M KCl containing 0.01 M HEPES buffer, pH=7.4). All three current traces were obtained at the same applied potential and are shown with the same scaling of the y- and x-axis.

The details of one or more embodiments of the invention are set forth in the accompanying drawings and the description below. Other features, objects, and advantages of the invention will be apparent from the description and drawings, and from the claims.

General biosensor and membrane technology and particularly ion-channel switch biosensors are described in U.S. Pat. Nos. 5,443,955; 5,741,409, and 5,741,712; the contents of which are incorporated herein by reference.

In order to provide a clear and consistent understanding of the specification and claims, including the scope given to such terms, the following definitions are provided:

As used herein, "admittance" refers to an electrical term used to describe the ability of ions to transverse a system when a potential is applied, and is expressed as units of Siemen (S) or Mho (inverse of Ohm). Admittance is the reciprocal of impedance.

As used herein, "an amphiphilic molecule" refers to a molecule having a hydrophilic head portion and one or more hydrophobic tails.

As used herein, "conjugate" refers to a chemical compound that has been formed by the joining or attachment of two or more compounds. Accordingly, an "ionophore conjugate" as provided herein includes ion channel forming peptides modified to include a charge-modifiable substrate.

As used herein, "impedance" is a general expression applied to any electrical entity that impedes the flow of ions. Impedance is used to denote a resistance, a reactance, or a combination of both reactance and resistance, with units of Ohm ($\Omega$).

As used herein, "ionophores" refer to natural or synthetic substances that promote the passage of ions through lipid barriers in natural or artificial membranes. Ionophores may form ion-conducting pores in membranes.

As used herein, "a spacer group" is a chemical group that links an ionophore and a reactive moiety.

As used herein, "substrate" is a molecule that contains a moiety that can be modified by a target analyte such that the charge of the substrate is altered. A moiety can be a charged group, such as a phosphate group, the removal of which alters the charge of the substrate. Alternatively, a moiety can be a chemical group suitable for attaching a charged group. For example, a moiety that can be phosphorylated by a target analyte may be used in the present compositions and methods.

Provided herein are ionophore conjugates that include an ion channel forming peptide associated with a substrate. The charge of the substrate is modifiable such that a change in the substrate charge detectable impacts the flow of ions through the channel. The present invention is further directed to a membrane inserted with such a conjugate in which the admittance of the membrane is dependent on the presence or absence of an analyte.

Ionophores of the present invention are in general peptides capable of forming helices and aggregates thereof, podands, coronands and cryptands. Podands, cryptands and coronands have been described previously in the scientific literature (see, for example, V. F. Kragten et al., J. Chem. Soc. Chem. Commun., 1985, 1275; O. E. Sielcken, et al., J. Amer. Chem. Soc., 1987, 109 4261; and J. G. Neevelk, et al., Tetrahedron Letters, 1984, 25, 2263). It is preferred that the ionophore is a peptide capable of forming a helix or aggregates thereof.

Peptides that form helices generally exist as aggregates in the membrane to form ionophores. Typically, helical peptides arrange to form aggregates in such a manner that an ionophore is created through the aggregate. Ionophores useful for the present invention include both transmembrane and dimeric ionophores, such as gramicidin, band three protein (Cell Mol. Biol., 2004; 50(2): 117-38), bacteriorhodopsin (Ann. Rev. Biophys. Biomol. Struct., 1999; 28:367-99) proteorhodopsin (EMBO Journal, 2003; 22:1725-1731), mellitin (Biochem. Biophys. Acta, 1983; 732 668-674), alamethicin (Journal of Lipid Research, 1973; 14: 255-a-257), an alamethicin analogue, porin (PNAS, 2002; 99:13108-13113), tyrocidine (J. Biol. Chem. 1979; 254: 6278-6287), tyrothricin (European Journal of Clinical Microbiology & Infectious Diseases, 1996; 15: 261-263) and valinomycin (Journal of General Physiology, 1981; 77:387-417).

Gramicidins include gramicidin A, gramicidin B, gramicidin C, gramicidin D, gramicidin GT, gramicidin GM, gramicidin $GM^-$, gramicidin $GN^-$, and gramicidin A'. Gramicidin A is particularly useful in the present invention. Gramicidin A is a peptide that forms a .beta. helix. The primary sequence of gramicidin A is described in U.S. Pat. No. 5,741,712. Gramicidin A is produced either synthetically or extracted from *Bacillus brevis*. Gramicidin A functions as a polar channel that traverses non-polar biological membranes. In phospholipid bilayers, gramicidin A is believed to exist as a helical dimer, which substantially partitions into the hydrophobic region of the bilayer.

An ionophore conjugate may include a spacer group. The spacer group can be hydrophilic (having a tendency to bind or absorb water) or hydrophobic (antagonistic to water and incapable of dissolving in water). The ionophore and the spacer group can be linked by any suitable moiety such as an ester, amide, carbamate, carbonate, or the like. In general, the target analyte may be an enzyme that modifies a moiety associated with the substrate such that the charge of the substrate is changed.

The admittance of the membrane containing an ionophore conjugate described herein is responsive to the target analyte modifying the charge of the substrate associated with the ion forming peptide. In one embodiment, the first state of the substrate is a state in which the passage of ions through the ion channel is prevented or hindered. Association of the target analyte to the substrate causes the substrate to enter a second state (e.g., charged or uncharged) wherein ions may pass through the ion channel. In this arrangement, an ion channel may be used to detect as little as a single molecule of analyte. The attachment of a single molecule of analyte will cause an ion channel to open and thus cause a leak of ions across the membrane. After a brief time, this ion leak may be detected as the signal for the binding of the analyte to the recognition molecule.

In another embodiment, the first state of the substrate is a state in which the passage of ions through the ion channel is allowed. Attachment of the target analyte to the substrate causes the recognition molecule to enter the second state wherein the passage of ions through the ion channel is hindered. The measurement of current flow across membranes due to a single ionophore typically yields a current of about 1-10 pA per channel and preferably.

Methods for measuring the change in admittance or impedance of membranes are comprehensively described in the scientific literature. One method involves the use of black lipid membrane chambers. The method of signal analysis can be a two, three or four terminal impedance measurement in which the frequency characteristics, noise spectra, cyclic voltammetry or statistics on the inherent making or breaking of ion channels are used to characterize changes in admittance through the membrane (see U.S. Pat. No. 5,741,712).

The present invention is also directed to a biosensor comprising the membrane as described above and a solid surface, wherein the membrane is attached to the solid surface in a manner such that a reservoir exits between the membrane and the solid surface. The reservoir serves as a zone or space wherein conductive ions can accumulate. The solid surface is in general conductive and serves as an electrode.

In one embodiment, the membrane is attached to a solid surface via reactive groups on the amphiphilic molecules in the first layer of the membrane. Solid surfaces include hydrogels, ceramics, oxides, glasses, silicon, polymers, and transition metals. Preferred transition metals are gold, platinum and palladium. The attachment of the membrane to a solid surface can be achieved by non-covalent or covalent attachment. For example, vinyl groups on a solid substrate can be copolymerized with a vinyl-terminated lipid. A sulfur-terminated lipid can be adhered to a metal (e.g. gold or palladium) substrate. Condensation or addition reactions can be used to anchor the lipid onto a solid surface. Modification of the solid substrate, if necessary, can be achieved using known techniques such as silylation. Methods of attaching membrane to the solid surface are described, for example, in U.S. Pat. No. 5,741,409, which is incorporated herein by reference.

The biosensor of the present invention can be constructed in a similar fashion as to those described in U.S. Pat. Nos. 6,291,155; 5,401,378; and U.S. Pat. No. 6,316,273; the contents of which are incorporated herein by reference.

Tethering a lipid bilayer membrane to an electrode such as a gold electrode provides enhanced stability of a biosensor. Unlike a conventional supported lipid bilayer, a tethered system allows the system to be formulated for an extended storage. The lipid tethering also allows high detection sensitivity due to an ionic reservoir region formed between an electrode and the tethered lipids. Ion flux between the reservoir and the external compartment allows convenient electrical transduction measurement in multi-sensor array format.

The biosensor provides a tool for detecting the presence or absence of a target analyte in a sample. In one embodiment, the present invention provides a method for detecting the presence or absence of an analyte in a biological sample. In some embodiments, admittance or impedance is determined at various intervals after the contacting, for example, at intervals of seconds or minutes when the binding reaction between the analyte and recognition molecule is in still progress and is not complete. In other embodiments, impedance or admittance is determined when the binding reaction reaches equilibrium or a plateau. The measurement of the change in admittance or impedance is influenced by the affinity of the target analyte to the substrate. In some embodiments, the contacting time will be for seconds or minutes and the determination of admittance or impedance is made at intervals of seconds or minutes.

Samples that will include a target analyte, and are suitable for the present invention include body samples and non-body samples. Examples of body samples are blood, serum, sweat, tears, urine, saliva, throat swabs, nasopharyngeal aspirates, smears, bile, gastrointestinal secretions, lymph, and organ aspirates and biopsies. Non-body samples include any solution samples not derived from a human body, for example, culture medium, water, saline, organic acids and buffers. A wide variety of analytes such as hormones, proteins, nucleic acids, drugs, small molecules, microorganisms, electrolytes, antigens, and antibodies can be detected or quantitated by the present invention. The present invention provides a rapid, sensitive, specific, and reproducible method for detecting an analyte.

The present invention is further directed to a device comprising an array of biosensors as described throughout the present application. Because biosensors measure electrical transduction signals, miniaturization of the device is achievable. The device is useful in that it can measure multiple samples at the same time. In one embodiment, the various biosensors can be arranged within a single device containing identical membranes, and are used to detect the same target molecule (analyte) from various samples. In another embodiment, the various biosensors can be arranged within a single device containing different membranes, and are used to detect a panel of different analytes either from the same sample or from different samples.

The disclosure is illustrated in the following examples, which are provided by way of illustration and are not intended to be limiting.

EXAMPLE 1

Figure 2:
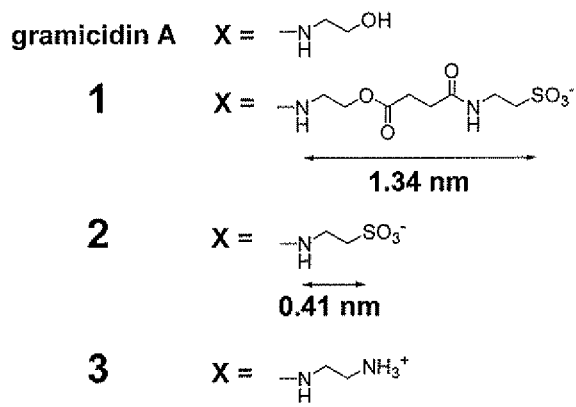
FIG. 2 depicts the sequence and calculated structure of two negatively charged derivatives of gramicidin A (gA). A) Sequence of gA, of a negatively charged sulfonate group covalently attached to gA via a long spacer (1), a negatively charged sulfonate group covalently attached to gA via a short spacer (2), and a positively charged amine group covalently attached to gA via a short spacer (gramicidamine, 3). The lengths shown for the spacers in 1 and 2 (from the nitrogen atom to the sulfur atom) were estimated by energy minimization in their fully extended conformation. B) Computer-generated side view (left) and top view model (right) of 1 based on molecular mechanics calculations. C) Computer-generated side view (left) and top view model (right) of 2 based on molecular mechanics calculations.
Figure 2:
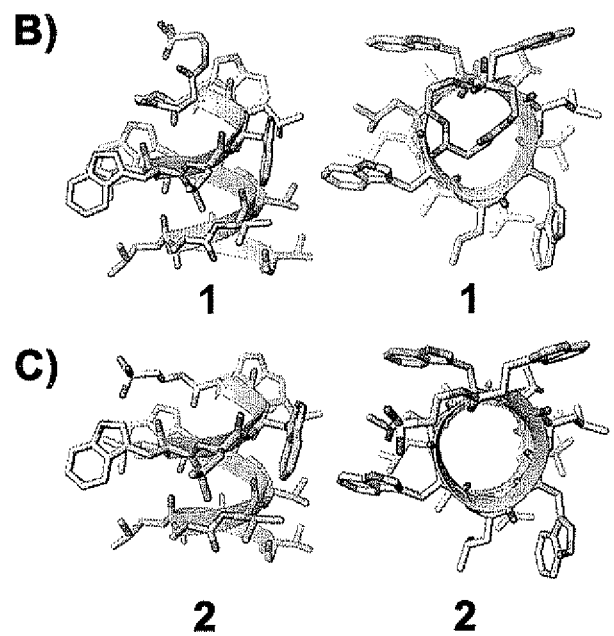

A) Influence of the distance of charged residues from the opening of the pore on the conductance of derivatives of gA: In order to investigate the influence of the distance of a charged group attached to the entrance of a gA pore on the single channel conductance, two sulfonate derivatives of gA were synthesized (FIG. 2A): one with a long spacer, 1; and one with a short spacer, 2. A sulfonate group was chosen for these studies because it maintains a constant negative charge over a wide pH range (since the pKa of a sulfonate group is <0). FIGS. 2B and 2C show the energy minimized structures of 1 and 2, respectively, as computed from a conformational search based on molecular mechanics calculations using Macromodel software. From the conformations shown in FIGS. 2B and 2C, the location of the negative charge in 1 and 2 was compared by measuring the distance of the sulfur atoms to a fixed point in space near the opening of the pore (located at half the distance between the a-carbon of Leu14 and the a-carbon of Trp11). From this comparison, the molecular mechanics calculations estimate that the sulfonate group of 1 is 0.75 nm and the sulfonate group of 2 is 0.68 nm from this fixed point at the opening of the pore. By measuring the distance of the sulfur atoms in 1 and 2 with the spacers in fully extended conformation it is possible to estimate the charge of the sulfonate group in 1 as located at a maximum distance of 1.81 nm and in 2 to be located at a maximum distance of 0.88 nm from this same fixed point near the opening of the pore. Although these charged derivatives of gA are likely to adopt dynamically a number of conformations with fluctuating distances of the charge from the pore when incorporated in a bilayer setup, these calculations are qualitatively consistent with the reasonable prediction that, on average, the charge in 1 is located further away (0.75-1.81 nm) from the opening of the pore compared to the charge in 2 (0.68-0.88 nm).

Figure 3:
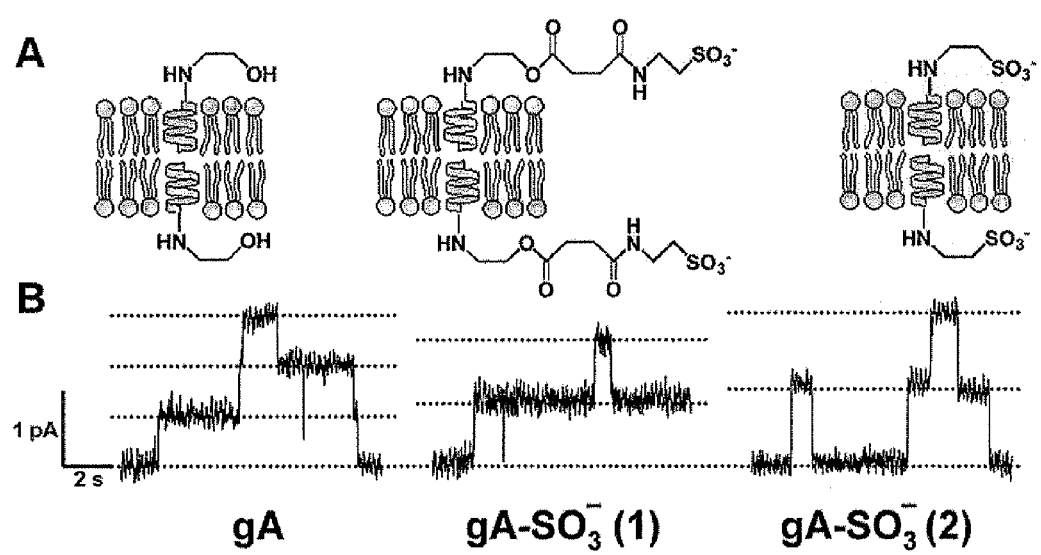
FIG. 3 depicts gA pores in planar lipid bilayers and current versus time traces of the respective dimeric pores. A) Cartoon representation of homodimeric pores of gA-gA, 1-1, and 2-2 in a bilayer and B) corresponding representative ion channel traces of pores of gA-gA, 1-1, and 2-2. All three traces were obtained at an applied potential of +150 mV from lipid bilayers made with 1,2-diphytanoyl-sn-glycero-3-phosphocholine (DiPhyPC) in an electrolyte containing 0.02 M KCl buffered with 0.2 mM HEPES at pH 7.4. Note the increased single channel conductance of pores of 1-1 compared to gA-gA and of 2-2 compared to 1-1 and gA-gA. All current traces are shown with the same scaling of y- and x-axis after low-pass filtering with a digital Gaussian filter with a cutoff frequency of 30 Hz.

FIG. 3 shows representative traces of the currents generated from different derivatives of gA at an applied potential of 150 mV in a recording buffer containing 0.02 M KCl: the difference in conductance of ions through pores formed from gA-gA, 1-1, or 2-2 resulted from the difference in magnitude (i.e., no charge versus negative charge) and distance of the charge attached near the entrance of the pore. These distinct conductance values are consistent with previous reports using derivatives of gA to detect chemical reactions that resulted in a difference in charge of functional groups attached to the opening of these pores.

FIG. 3 demonstrates that the conductances of pores of 1-1, and 2-2 are measurably different from the conductance of pores of gA-gA and illustrates that this difference is greater when the negative charge is located close to the entrance of the pore (2) compared to a charge that is located further away (1). According to the Debye-Hückel theory, the electrostatic attraction between oppositely charged species near a charged surface is distance dependent. In addition, this theory predicts that the electrostatic attraction of cations in solution by the negative sulfonate group in 1 and 2 decreases with increasing ionic strength of the electrolyte solution (due to the small double-layer thickness and the corresponding enhanced shielding of the negative charge in solutions with increased concentrations of ions). This was examined by comparing the ion channel conductance of gA, 1, and 2 in recording buffers with different ionic strengths.

B) Influence of the ionic strength of the recording buffer on the conductance of negatively charged derivatives of gA: Table 1 shows the single-channel conductance of homodimers of gA and of negatively charged gA derivatives 1 and 2. The effect of the negative charge on the gA derivatives with respect to their single-channel conductance decreased with increasing ionic strength of the solution, as predicted by the Debye-Hückel theory. It was found that the greatest relative difference in conductance between homodimers of 2 and homodimers of gA when we used a buffer with a concentration of about 0.01 M KCl. At this concentration, the conductance of 2-2 was a factor of about 1.6 larger than that of gA-gA. Even at a concentration of about 0.10 M KCl, the single-channel conductance of 2-2 was a factor of 1.2 greater than the conductance of gA-gA. Alternatively, at a concentration of about 1.00 M KCl, the difference in single channel conductance between gA-gA and 2-2 was below approximately 10% (see Table 1). With regard to derivative 1 (with the negative sulfonate group attached to gA by a longer spacer length compared to 2) the effect of screening electrostatic attraction was more pronounced compared to gA derivative 2: at low ionic strength (0.01 M KCl) the difference in conductance compared to gA was greater by a factor of about 1.3, at approximately 0.10 M KCl and approximately 1.00 M KCl the difference was 7% and 3%, respectively. For these sulfonate derivatives of gA, the difference in charge compared to gA appeared to dominate the single channel conductance over any other differences in chemical properties such as the size (i.e., bulkiness) of the attached group. Based on the results from Table 1, KCl concentrations lower than about 0.01 M may further enhance the difference in conductance between the negatively charged gA derivatives and the original, uncharged gA. In order to obtain reliable and reproducible recording conditions, KCl concentrations of at least about 0.01 M (preferably ≥0.02 M) worked efficiently for the ion channel experiments described in the present application. The experiments shown in Table 1 were conducted by using "folded" and "painted" bilayers. There were no significant differences in conductance of the pores, however, the average relative standard deviation of the conductances was smaller in folded bilayers than in painted bilayers (2.4% versus 5.5%). This difference is expected since folded bilayers are "solvent-free", more precisely; decane is typically replaced by hexadecane, which partitions less into the bilayer than decane and thus folded bilayers result in thinner membranes that are typically considered better models of biological bilayers than painted bilayers. Therefore, in order to maximize the sensitivity of sensors that measure changes in the single channel conductance of gA, folded bilayers are preferable. It is, however, possible to use painted bilayers if sensor simplicity is important.

C) Importance of a well-defined charge on the derivative of gA in the pH range of nalysis: Since the charge on functional groups attached to gA may depend on the protonation state of the molecule, it is important to consider the pKa of functional groups in the design of a charge-based gA sensor. To demonstrate the importance of a well-defined charge on the gA derivative at the pH range of analysis, the conductance of pores from 2-2 was compared with the conductance of pores from gA-gA at pH 7.4 and pH 12 (Table 2). The conductance of pores from 2-2 was significantly larger than the conductance from gA-gA at both pH values (due to the presence of the sulfonate group on 2, which was charged negatively at both pH values since its pKa in water is <0). To provide an example of a functional group whose charge is not well-defined over the same pH range, an amine-terminated derivative of gA was synthesized (gramicidamine; group 3 of FIG. 2). This derivative of gA is expected to be predominantly protonated (and hence positively charged) at pH 7.4 and predominantly uncharged at pH 12 (since the pKa of a primary amine in water is ~10). When the conductance of pores from 3-3 were compared with the conductance of pores from gA-gA at pH 7.4 (Table 2), it was found that the conductance of 3-3 was significantly less than the conductance of gA-gA. In contrast, at pH 12, the predominant conductance of 3-3 was indistinguishable from the conductance of gA-gA (presumably due to the neutral character of the unprotonated amine group). These results demonstrate the importance of designing charge-based sensors such that there is a measurably different conductance between the two derivatives of gA at the operational pH.

Figure 4:
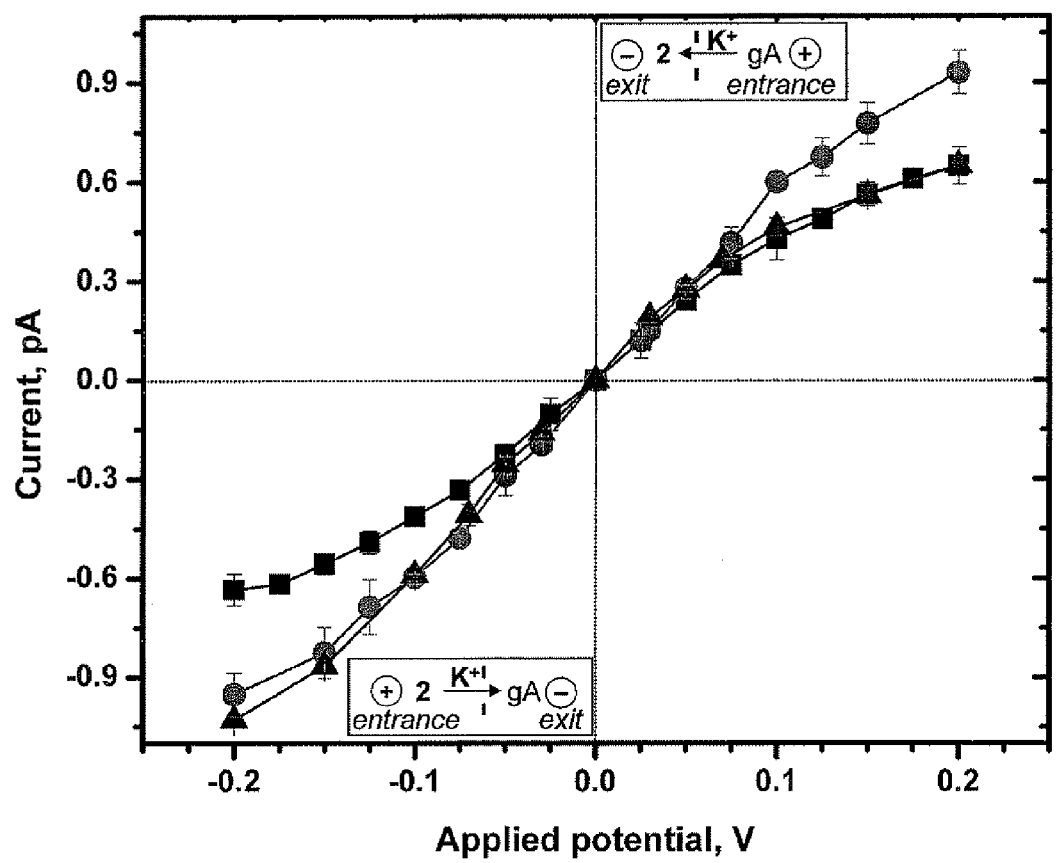
FIG. 4 depicts current-voltage characteristic of a homodimeric pore of gA-gA (■), 2-2 (●), and a heterodimeric, asymmetric pore of gA and 2 (▲). The heterodimeric, asymmetric pore was assembled by adding native gA to the cis compartment and 2 to the trans compartment of the bilayer setup (44) (the cis compartment refers to the compartment that defined the polarity of the applied voltage, the trans compartment was connected to ground). The concentration of KCl was 0.02 M for these experiments and bilayers were formed with DiPhyPC lipids using the folding method. Each data point represents the average of at least three measurements of current. (66) The annotations of gA and 2 in the boxes of the graph indicate the direction of the flux of $K^+$ ions (arrows) and thus illustrate whether gA or 2 was at the entrance or at the exit of the pore at a given polarity of the applied voltage.

D) Dependence of the current-voltage characteristic of gA channels on the applied transmembrane voltage and on the molecular heterogeneity of the gA dimmers: FIG. 4 Demonstrates that the absolute difference in conductance between gA and its negatively charged derivative 2 increased with increasing transmembrane potential in a recording buffer containing 0.02 M KCl. FIG. 4 also shows that the current through all gA pores did not increase linearly with applied voltages above 100 mV. This nonlinear behavior was observed at low KCl concentrations (≤0.10 M KCl). At a concentration of about 1.00 M KCl, the I-V curve of gA was linear. One possible explanation for the non-linear behavior of the I-V curve of gA and its negatively-charged derivatives at low KCl concentrations is that the flux of ions through the pore was sufficiently fast that the supply of potassium ions to the pore started to become rate limiting at high applied potentials (>100 mV) for the overall rate of ion transport. The mass transport limited maximum current through a gA pore (diameter~4 Å) was approximated as the diffusion limited current that can be measured by a disk-shaped nanoelectrode (with a radius $r=2\times10^{-10}$ m) due to the reduction or oxidation of an electroactive species (with one transferred electron per reaction, n=1). In analogy to the electroactive species reacting instantaneously at the nanoelectrode surface, it is assumed that K+ ions that reach the opening of gA pore are instantaneously driven through the pore by the applied electric field. Using a concentration of $c=20$ mols $m^{-3}$ (20 mM) K+ ions that have a diffusion constant of $D=1.96 \cdot 10^{-9}$ $m^2$ $s^{-1}$ and an equation that describes the steady state limiting current (i) of a nanodisk electrode: $i=4nFDcr$ where $F=96,485$ C is the Faraday constant (from Bard, A. J. and Faulkner, L. R. Electrochemical Methods, Fundamentals and Applications, John Wiley & Sons, 2nd Ed., 2001, p. 171), it was predicted that the maximum achievable, mass transport limited current through a gA pore in a solution with 20 mM K+ ions is~3 pA. Since this maximum current will be approached asymptotically with increasing potentials, it is reasonable that the measured currents will deviate from ohmic behavior (current=applied potential×conductance) at potentials that are not sufficiently large to reach this mass transport limited current of 3 pA (for instance, at 200 mV applied potential in FIG. 4, the current through 2-2 was~30% of this estimated maximum, mass transport limited current).

A negatively charged group that is able to increase the local concentration of potassium ions close to the entrance of the pore due to electrostatic attraction results in an increase in conductance compared to native gA under the same applied potential. This increase was most pronounced at low ionic strength of the bulk solution (here at low concentration of KCl) and under conditions where the supply of ions to the pore is starting to become a limiting factor (for example at high transmembrane voltages when the movement of the ions through the pore is sufficiently fast). The results provided in FIG. 4 exemplify the relative difference in conductance between the negatively-charged gA derivatives compared to gA increased with increasing transmembrane voltage; the ratio between the conductance of 2-2 and gA-gA (at a KCl concentration of 0.02 M), for instance, increased from 1.4 at 100 mV to 1.5 at 200 mV applied potentials.

Sensors based on changing the charge of chemical groups attached to the entrance of a gA pore were constructed. gA derivatives that include charged or uncharged gA monomers in a dimeric pore were identified in order to observe a measurable change in conductance. The conductance behavior of a heterodimeric gA pore (see e.g., FIG. 4) was performed. Asymmetric heterodimeric pores were composed of gA in one leaflet of the bilayer (here, the leaflet facing the aqueous compartment that defined the polarity of the applied voltage, denoted as the cis compartment) and of 2 in the opposite leaflet of the bilayer (denoted as the trans compartment). The data shown in FIG. 4 indicates that at transmembrane potentials above 100 mV, the I-V characteristic of heterodimeric pores was dominated by the charge on the gA derivative that was located at the entrance of the pore; it was not substantially affected by the charge on the gA derivative at the exit of the pore. The data indicates that if the polarity of the applied potential was such that the negatively charged gA derivative 2 was located at the entrance of the pore for K+ ions (i.e., 2 added to the positively-polarized compartment) while native gA was located at the exit of the pore (i.e., gA added to the negatively-polarized compartment), then the overall conductance was approximately the same as that of homodimeric pores from 2. Switching the polarity and thus placing 2 at the exit of the pore and gA at the entrance of the pore resulted in a single-channel conductance that was similar to homodimeric pores of gA.

Molecule 2, in a heterodimeric pore, will, according to Debye-Hückel theory, increase the local concentration of K+ ions close to the side of the pore that is made up by 2. The gA molecule in the heterodimeric pore in the opposite leaflet of the bilayer, will not, however, influence significantly the local concentration of K+ ions near the membrane (since gA is not charged). Hence, if the polarity of the electric field is such that 2 is located at the entrance of the heterodimeric pore, the local increase in K+ ions will result in an increased conductance and the ensuing conductance can be expected to be similar to homodimeric pores of 2-2. Alternatively, if the polarity of the electric field is such that gA is located at the entrance of the heterodimeric pore, the concentration of K+ ions at the entrance is not increased and the conductance of such a pore can be expected to be similar to homodimeric pores of gA-gA. The data in FIG. 4 agrees with the predictions of this model.

Figure 5:
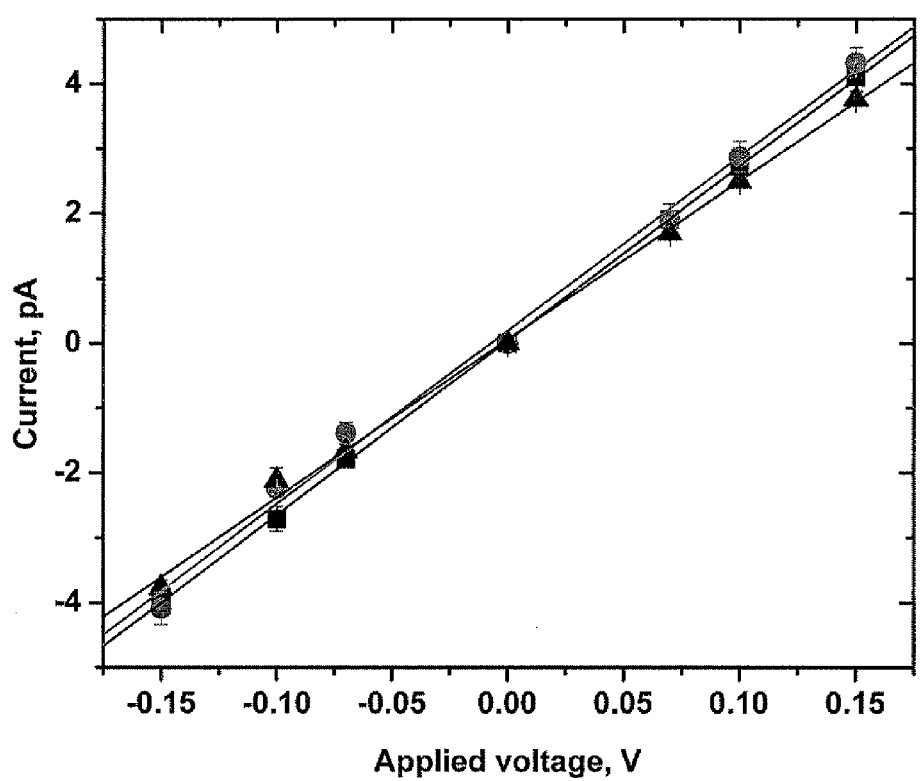
FIG. 5 depicts the effect of charge on the head group of the lipids in planar bilayers. Current-voltage characteristics of homodimeric pores of gA (■), 1 (●) and 2 (▲) in negatively charged bilayers at low ionic strength. Planar bilayers were made with 50% zwitterionic 1-palmitoyl-2-oleoyl-sn-glycero-3-phosphoethanolamine (POPE) and 50% negatively charged 1,2-dioleoyl-sn-glycero-3-phospho-L-serine (DOPS). All experiments were performed in 0.01 M KCl with 0.1 mM HEPES (pH=7.4) as electrolyte. Each data point represents the average of at least three mean current values calculated from fitting a Gaussian distribution to histograms of the current from original current versus time traces.

E) Influence of charge on the lipid headgroups on the single channel conductance of gA and its derivatives: In order to investigate the single channel conductance of the different gA derivatives in neutral, negatively charged, and positively charged planar bilayers in the lowest possible KCl concentration, bilayers in about 0.01 M or 0.02 M KCl were formed. As shown in FIG. 5, the negative charges on the headgroups of lipids in bilayers significantly neutralized the difference observed in FIG. 4 in single channel conductance between gA-gA, 1-1, and 2-2. The differences in conductance measured for 2-2 ($\gamma=24.4\pm0.5$ pS) compared to gA-gA ($\gamma 26.9\pm0.2$ pS) or 1-1 ($\gamma=26.8\pm0.9$ pS) when measured in bilayers containing lipids with negatively charged headgroups is likely due to differences in chemical/physical properties other than charge (e.g., bulkiness). Since the relatively bulky sulfonate group in 2 is located closer to the opening of the pore compared to in 1 (e.g., see FIG. 2), one might expect a slightly reduced conductance of ions through channels of 2-2 compared to 1-1 or gA-gA under experimental conditions in which the effect of the charge on the sulfonate groups on 1 and 2 is overridden by the negative charges of the lipids in the membrane.

FIG. 5 demonstrates that negative charges on the lipid membrane can override the effect of the negative charge on the sulfonate group of derivatives 1 or 2 even at concentrations of low ionic strength (here, 0.01 M). Alternatively, in bilayers that were made with neutral (zwitterionic) DiPhyPC lipids, the single channel conductance of 2-2 was significantly different from the conductance of gA-gA pores at low ionic strength (see Table 1). Only at high ionic strength (1.00 M KCl) were the conductances of pores of 2-2 in zwitterionic lipid membranes approximately the same the as pores of gA-gA.

With regard to the conductance in negatively charged membranes (50% DOPS, 50% POPE), it is noted that the conductance values of homodimers of gA and its derivatives are increased compared to zwitterionic membranes. This observation is consistent with the prediction that permanent negative charges near the entrance of the pore increase the local concentration of cations. This increase in concentration results in increased flux of K+ ions through the pores and this effect can be caused by charges at the entrance of the pore such as in 2 or by charges on the surrounding membrane lipids close to the entrance of the pore.

FIG. 5 shows that, at a concentration of about 0.01 M KCl, the effect of electrostatic attraction of ions to the bilayer predicted by the Debye-Hückel theory is very strong to the point that the conductance of gA-gA pores (27 pS) in 50% DOPS bilayers is higher than the conductance of gA-gA (20 pS) in zwitterionic bilayers made with DiPhyPC in a electrolyte containing 1.00 M KCl.

The conductance of gA-gA and 2-2 in lipid bilayers that contained 10% of a lipid with positively-charged headgroups (here, 1,2-dioleoyl-3-(dimethylamino)propane, DODAP, and 90% DiPhyPC) was measured. It was found that the relative ratio of conductance of 2-2 to gA-gA was 10% larger than the relative ratio of conductance of these two homodimeric ion channels in purely zwitterionic lipids (both were measured in 20 mM KCl). These results show that using membranes that are oppositely charged than the gA derivatives makes it possible to enhance the relative difference in conductance between the charged and uncharged pores compared to measurements in zwitterionic lipids.

Thus, to increase the effect of the change in charge of gA derivatives for sensor applications, the lipid headgroups in the bilayers may be zwitterionic or oppositely charged than the gA derivatives used for sensing.

The examples presented herein demonstrate that gA-based ion channels are an excellent platform for development of sensors. Specifically, gA is readily available in gram-scale quantities, (42) it is conducive to synthetic derivatization, and it is simple to use due to its spontaneous self-incorporation into bilayers and its discrete conductance values. In addition, assays based on gA can be inexpensive, amenable to miniaturization, and potentially portable.

Materials: All reagents and chemicals were purchased from Sigma-Aldrich unless otherwise stated. Gramicidin A (gA) was purchased from Cal Biochem (97% purity). The following lipids were purchased from Avanti Polar Lipids, Inc.: 1,2-diphytanoyl-sn-glycero-3-phosphocholine (DiPhyPC); 1,2-dioleoyl-sn-glycero-3-[phospho-L-serine] (DOPS); and 1-palmitoyl-2-oleoyl-sn-glycero-3-phosphoethanolamine (POPE) and 1,2-dioleoyl-3-dimethylammonium-propane (DODAP).

Synthesis of gramicidyl taurinyl succinate (1): We dissolved 6 mg of gramicidin A (gA) (3.2 µmol) in 0.5 mL of dichloromethane (DCM). We added 2.6 µL (32 µmol) of pyridine and 3.2 mg (32 µmol) of succinic acid to the solution of gA. To increase the solubility of succinic acid, a few drops of tetrahydrofuran (THF) were added. The solution was stirred for 12 h at 23° C. After concentrating the solution en vacuo, the desired product was isolated by chromatography over silica using a 9:1 mixture of DCM/methanol (MeOH) as eluent. The desired product had an Rf value of 0.3 (for comparison, gA had an Rf value of 0.5) using the same eluent. The product was taken directly to the next step without further characterization.

We dissolved 2.6 mg (1.3 µmol) of gramicidyl succinic acid and 0.17 µL (1.3 µmol, from a stock solution in THF) of tert-butyl chloroformate in 1 mL of anhydrous THF. The solution was stirred for 10 min at −20° C. Then 0.15 µL (1.3 µmol, from a stock solution in THF) of diisopropylethylamine was added and the flask was flushed with N2. The reaction was stirred at 0° C. for 30 min, and 0.02 mL of an aqueous 16 mg mL-1 solution of taurine (2.6 µmol) was added to the mixture. The mixture was stirred at 0° C. for 3 h, warmed to 23° C. and then stirred for an additional 10 h. The solution was concentrated en vacuo and the product was isolated in 28% yield by chromatography over silica using a 9:1 mixture of DCM/MeOH as eluent. The desired product had an Rf value of 0.1 in the same eluent. ESI-MS showed a peak at m/z=2090.48 corresponding to the expected [M+H]+ of 1.

Synthesis of taurinyl gramicidate (2) and gramicidamine (3): We prepared 2-aminoethyl gramicidate using a modified procedure that was previously reported in the literature (Rambhav et al., J. Biochem. Biophys. 1972, 9, 225-229). We dissolved 12.35 mg (6.3 µmol) of gA in 0.25 mL of anhydrous acetonitrile. We added 25 µL (260 µmol) of POCl3 to the solution of gA. The reaction was stirred at 23° C. for 4 h. The solution was concentrated en vacuo. The mixture was then dissolved in 1 mL of 10% H2O in acetonitrile and stirred for 30 min. After concentrating the solution again en vacuo, the mixture was dissolved in 1.5 mL of 2:1 DCM/MeOH and the resulting solution was added dropwise to 50 mL of H2O. The precipitate was collected on filter paper to yield 97% of crude product based on gA. ESI-MS in negative mode revealed a major peak at m/z=1880.85 corresponding to the [M−H]− of the product.

We dissolved 5.2 mg of crude 2-aminoethyl gramicidate in 0.15 mL of acetonitrile and 0.45 mL of acetate buffer (0.5 M, pH=3.9) and stirred for 5 min at 23° C. We added 30 mg NaNO2 to the solution and the reaction was stirred for 7 h at 23° C. The mixture was concentrated en vacuo and dissolved in 0.5 mL of 2:1 DCM/MeOH. The solution was added dropwise to 50 mL of H2O. The resulting precipitate was collected to yield 95% of crude product based on 2-aminoethyl gramicidate. ESI-MS in negative mode showed a major peak at m/z=1881.68 corresponding to [M−H]− of the product.

We dissolved 4 mg (2.1 µmol) of 2-hydroxyethyl gramicidate in 292 µL MeOH. Separately, 15.4 mg (47.5 µmol) of Cs2CO3 was dissolved in 126 µL of $H_2O$ and this aqueous solution was added to the solution of 2-hydroxyethyl gramicidate. The reaction was stirred for three days at 23° C. The solution was concentrated en vacuo, dissolved in 9:1 DCM/MeOH, and added dropwise to 50 mL of H2O. The resulting precipitate was isolated to yield 97% of crude product based on 2-hydroxyethyl gramicidate. ESI-MS in positive mode revealed a major peak at m/z=1836.61 corresponding to the expected [M+H]+ of the product.

Synthesis of taurinyl gramicidate (2): We dissolved 4 mg (2.2 µmol) of desethanolamine gramicidin in 0.3 mL of THF. We added 34.1 µL (237.6 mmol) of $Et_3N$ and flushed the flask with $N_2$. The reaction vessel was cooled to 0° C. and 1.2 µL of ethyl chloroformate was added. The solution was stirred at 0° C. for 3.5 h and then a solution of 1.65 mg of taurine (dissolved in 30.0 mL of $H_2O$) was added to the solution containing desethanolamine gramicidin. The reaction was stirred for 30 min at 0° C., warmed to 23° C., and stirred an additional 12 h. The solution was concentrated en vacuo and purified by silica chromatography (9:1 DCM/MeOH) to give an overall isolated yield (over 4 steps) of 41% relative to gA. ESI-MS revealed a major peak at m/z=1944.79 corresponding to the expected [M+H]+ of the product.

Synthesis of gramicidamine (3): Desethanolamine gramicidin A (5 mg, 2.7 µmol) and triethylamine (4.4 µL, 30 µmol) were added to 0.2 mL of dry DCM and the resulting mixture was stirred and cooled to 0° C. After adding ethyl chloroformate (1 µL, 10.8 µmol) to the cooled mixture, the reaction was stirred for 3.5 h at 0° C. Mono-tert-butyloxycarbonyl-protected (BOC-protected) ethylenediamine was dissolved in 0.1 mL of dry DCM and cooled to 0° C. and added to the desethanolamine gramicidin mixture. The resulting mixture was stirred for 30 min at 0° C. and then at room temperature for 8 h. After concentrating to dryness, the BOC-protected gramicidamine was purified using preparative silica chromatography (9:1 DCM:MeOH as eluent). ESI-MS in negative mode showed a major peak at m/z=1979.66 corresponding to the expected [M−H]− of the product.

A mixture of 1 mL of 1:1 DCM:trifluoroacetic acid (TFA), 0.1 mL dimethylsulfide and 0.02 mL ethanedithiol was cooled to 0° C. BOC-protected gramicidamine (2 mg, 1 µmol) was added to this DCM:TFA mixture. The reaction was allowed to warm up to room temperature and stirred for 3 h. The solvent was evaporated and the crude mixture was dissolved in 2 mL of 2:1 DCM:MeOH. The mixture was added dropwise to 100 mL of water while stirring at 25° C. The resulting precipitate was collected by filtration. ESI-MS showed a major peak at m/z=1881.62 corresponding to the expected [M+H]+ of the product. The overall yield of 3 was 74% from desethanolamine gramicidin A.

Molecular modeling: The molecular mechanics calculations shown in FIG. 2 were performed using MacroModel (version 7.5, Schroedinger, Inc.) with energy minimizations (using MM2 force field parameters) in water. It is known in the art that charged derivatives of gA generally do not cross lipid bilayers. This characteristic is attributed to the energetic cost of exposing a charge to the hydrophobic core of a bilayer. Therefore, the negative charge of the sulfonate group favors an aqueous environment energetically over the hydrophobic bilayer environment. It is also known that gramicidin pores promote thinning of bilayers and therefore the C-terminus of gA should be accessible to an aqueous environment. Accordingly, the energy minimized structures were calculated in water.

We constructed 1 and 2 in silico by modification of the C-termini of the crystal structure of gA (1GRM) in Macro-Model. The first 14 residues of the peptide were fixed during the conformational analyses since they represent residues most likely embedded in the bilayer. After performing 5000 iterations of conformational analyses each for 1 and 2, we examined the structures of the 20 lowest energy conformations calculated for 1 and 2 and found they were all very similar to the structures shown in FIG. 2. We estimated the distance from the pore of the negative charge in 1 and 2 by measuring the distance of the sulfur atoms to a fixed point in space near the opening of the pore (located at half the distance between the a-proton of Leu14 and the a-proton of Trp11). To determine the maximum distance that the charge can exist from the pore in 1 and 2, we created a hypothetical structure in silico for 1 and 2 with spacers (FIG. 2A) in their fully extended conformation and measured the distance between the sulfur atoms and this same fixed point in space near the opening of the pore.

Formation of planar lipid bilayers: We formed most planar lipid bilayers with the "folding technique." We used a Teflon film (Eastern Scientific Inc, pore diameter 0.18-0.25 mm) was pretreated on each side with 2.5 µL of 5% hexadecane in pentane and air dried. This film was mounted using vacuum grease (Dow Corning, High vacuum grease) to a custom made Teflon chamber separating two buffer compartments each with a volume capacity of 4 mL. After adding 1 mL of electrolyte (0.01 M to 1.00 M KCl buffered with HEPES pH 7.4) to each compartment, lipids were spread from a solution in pentane onto the surface of the electrolyte solutions (specifically, 4-6 µL from 25 mg mL-1 solution DiPhyPC or from 6.25 mg mL-1 each of 50% DOPS and 50% POPE or from 25 mg mL-1 DODAP mixed with 25 mg mL-1 DiPhyPC in a 1:9 ratio. Three additional milliliters of electrolyte solution were added to each side of the chamber to raise the liquid levels above the aperture. We formed the bilayers from apposition of two monolayers of lipids using the method described by Montal et al. (Proc. Natl. Acad. Sci. U.S.A. 1972, 69, 3561-3566). Briefly, bilayers were obtained by consecutively raising the liquid level in each compartment until the pore was completely covered by electrolyte. If at this point the pore was not closed by a lipid bilayer, then the liquid level in one or both compartments was lowered below the pore level by aspirating electrolyte into a 3 mL syringe, followed by raising the electrolyte solution again. This cycle was repeated until a bilayer was obtained that had a minimum capacitance of 70 pF, and until the resulting membrane was stable (i.e., no significant current fluctuations above the baseline noise level) in the range of ±200 mV applied potential for several minutes.

Planar lipid bilayers were also made with the "painting technique". We pretreated each side of a pore in a bilayer cup (Warner Instruments, Delrin perfusion cup, volume 1 mL, pore diameter 250 µm) with ~2 µL of a 25 mg mL-1 solution of DiPhyPC in hexane. After adding recording buffer (0.01 M KCl to 1.00 M KCl buffered with HEPES, pH=7.4) to both compartments of the bilayer setup, we "painted" a solution of 20 mg mL-1 DiPhyPC in n-decane over the pore by using a paint brush with a fine tip. We followed the thinning of the decane droplet to form a planar bilayer by monitoring the capacitance of the bilayer. After verifying that bilayers were stable for several minutes (in the range of ±200 mV applied voltage) and that the capacitances were above 80-90 pF, gA was added (4-8 µL from 1 ng mL-1 in ethanol), derivatives 1 or 2 (2-10 µL from 100 ng mL-1 in ethanol), or derivative 3 (4-10 µL from 100 ng mL-1 in ethanol) directly to the bilayer chambers.

Ion channel measurements: We performed single channel recordings in "voltage clamp mode" using Ag/AgCl electrodes (Warner Instruments) in each compartment of the bilayer chambers. Data acquisition and storage was carried out using custom software in combination with either an EPC-7 patch clamp amplifier from List Medical Electronic (set at a gain of 100 mV pA-1 and a filter cutoff frequency of 3 kHz) or a Geneclamp 500 amplifier from Axon Instruments (with a CV-5B 100GU headstage, set at a gain of 100 mV pA-1 and filter cutoff frequency of 1 kHz). We used the EPC-7 amplifier for most folded bilayers and the Geneclamp 500 amplifier for most painted bilayers. The data acquisition boards for both amplifiers were set to a sampling frequency of 15 kHz. All current traces shown in the figures were further filtered using a digital Gaussian low-pass filter with a cutoff frequency of 30 Hz. The current traces we used to generate all data that was recorded at applied potentials s 50 mV were filtered at 10 Hz.

We performed the analysis of the single channel current traces by computing histograms of the currents from the original current-time traces with ClampFit 9.2 software from Axon Instruments. From these histograms we extracted the main current values by fitting a Gaussian function to the peaks in the histograms. All gramicidin molecules showed a predominant conductance and occasionally sub-conductance states (i.e. single channel currents that were smaller than the main current values). Single channel conductances reported in this paper always refer to the main conductance state (i.e. to the dominant peaks in the current histograms).

TABLE 1

Single-channel conductances, γ, of homodimers of gA-SO$_3^-$ with a long spacer arm (1) and of gA-SO$_3^-$ with short spacer arm (2) compared to native gA at different concentrations of KCl in the recording electrolyte (buffered with HEPES to pH 7.4).[a]

| Conc. of KCl (M) | γ gA-gA (pS) | γ 1-1 (pS) | γ 2-2 (pS) | γ-ratio 1-1/gA-gA | γ-ratio 2-2/gA-gA |
|---|---|---|---|---|---|
| 0.01 | 2.7 ± 0.5 | 3.5 ± 0.3 | 4.3 ± 0.3 | 1.3 | 1.6 |
| 0.10 | 10.3 ± 0.1 | 11.0 ± 0.4 | 12.6 ± 0.4 | 1.1 | 1.2 |
| 1.00 | 20.0 ± 0.2 | 19.5 ± 0.4 | 21.5 ± 0.3 | 1.0 | 1.1 |

[a]Bilayers were made from DiPhyPC lipids. Conductances were obtained from the slope of current versus voltage curves (I-V curves) in the linear range ≤|±100 mV| of the I-V curves. Errors represent the standard deviation calculated from at least two (typically three) independent experiments. 1 pS = 1 · 10$^{-12}$ Ω$^{-1}$. A two sample t-Test and a one-way ANOVA test both confirmed that (in recording buffer containing 0.01 M KCl and in recording buffer containing 0.10 M KCl) the mean conductance values of gA-gA, 1-1, and 2-2 were all significantly different from each other with a significance level of 0.05.

TABLE 2

Single-channel conductances, γ, of homodimers of gA, 2, and 3 at pH 7.4 and pH 12.[a]

| Composition of pore | γ at pH 7.4 (pS) | γ at pH 12 (pS) |
|---|---|---|
| gA-gA | 4.5 ± 0.1 | 7.8 ± 0.2 |
| 2-2 | 5.8 ± 0.1 | 9.8 ± 0.2 |
| 3-3 | 3.8 ± 0.2 | 7.7 ± 0.9 |

[a]Bilayers were made from DiPhyPC lipids in 20 mM KCl. For the measurements at pH 12, 10 mM KOH was added to this electrolyte to give the desired pH. Conductances were obtained from the slope of current versus voltage curves (I-V curves) in the linear range ≤|±100 mV| of the I-V curves.

Figure 7:
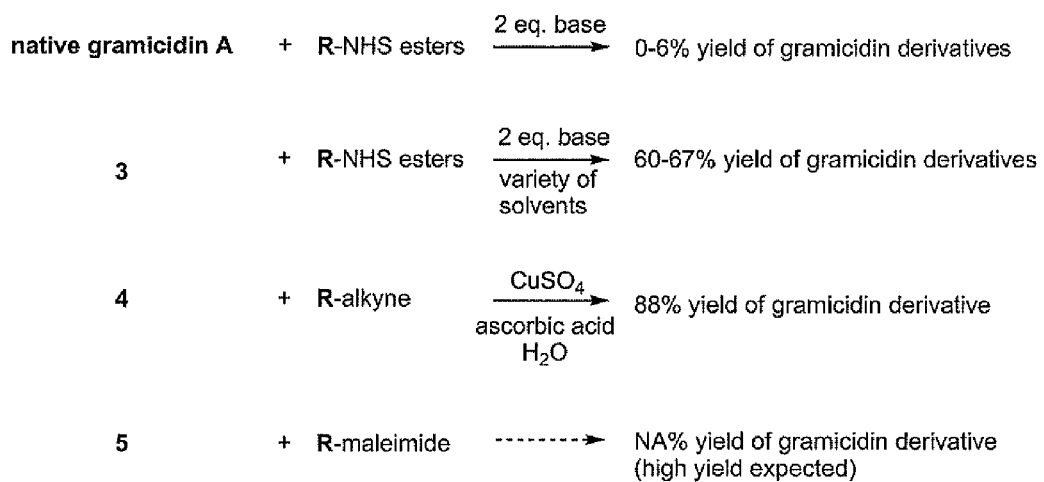
FIG. 7 provides samples of orthogonal reactivity of gramicidin analogs 1-3.
Figure 8:
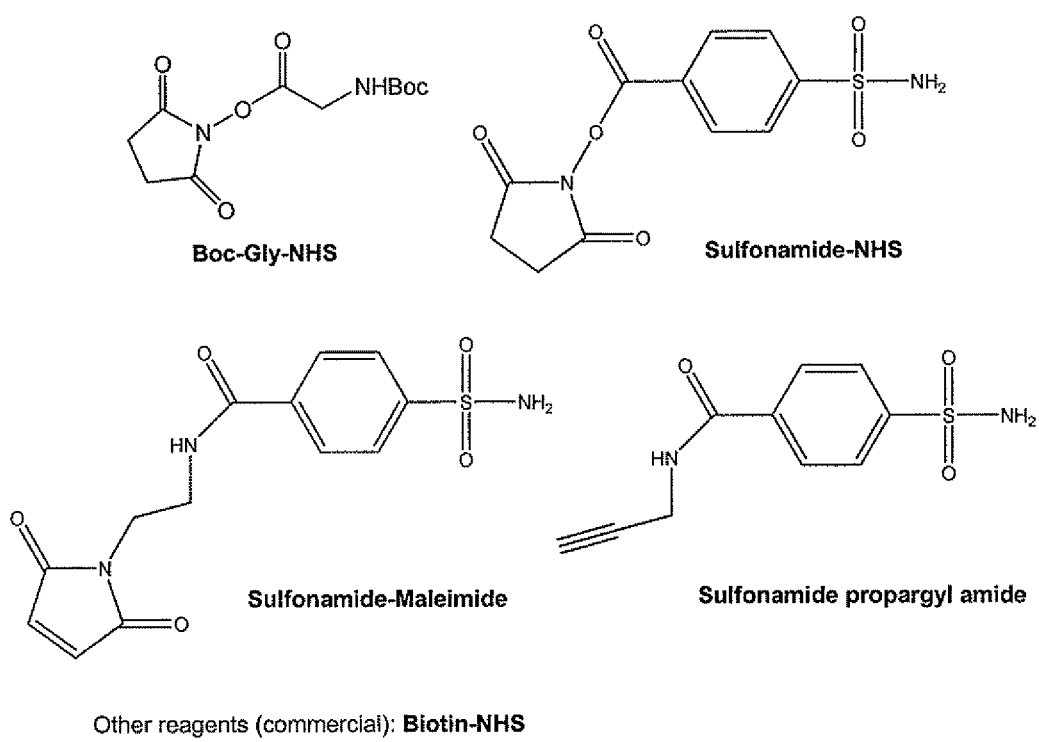
FIG. 8 presents reagents used to demonstrate the synthetic utility of the gramicidin derivatives 1-3, as shown in Table 3.

Synthesis of novel reactive analogs of gramicidin a (see also FIGS. 6-8 and Table 3): Gramicidin A (30 mg, 16 µmol) was added to 10 ml of acetonitrile. Phosphorus oxychloride (62.5 µL, 650 µmol) was added dropwise. The reaction stirred at room temperature for 4 hours. After concentrating the solid to dryness, 0.9 ml of acetonitrile and 2.7 ml of acetate buffer (pH 3.8) were added to the solid. Sodium nitrite (180 mg, 2.6 mmol) was added and the reaction was allowed to stir at room temperature for 7 hours. The reaction mixture was concentrated down and taken up in 3 ml of 2:1 methylene chloride:methanol. The mixture was added dropwise to a stirring beaker of 200 ml of water. The resulting precipitate was collected by filtration and dissolved in 2.25 ml of MeOH. A solution containing cesium carbonate (64.5 mg, 198 µmol) in 0.75 ml of water was added to the mixture. The solution was allowed to stir for 2 days at room temperature. 1 M HCl was used to adjust the reaction mixture's pH to 2. The reaction mixture was concentrated down and taken up in 3 ml of 2:1 methylene chloride:methanol. The mixture was added dropwise to a stirring beaker of 200 ml of water. The resulting precipitate was collected by filtration. ESI-MS shows a [M−H] fragment at 1837.69 and a retention time of 39.7 minutes. Overall yield was 89% from gramicidin A.

Synthesis of gramicidamine (FIG. 6, structure 3): Desethanolamine gramicidin A (5 mg, 2.7 µmol) and triethylamine (4.4 µL, 30 µmol) were added to 0.2 ml of dry methylene chloride and the resulting mixture was stirred and cooled to 0° C. After adding ethyl chloroformate (1.05 µL, 10.8 µmol) to the cooled mixture, the reaction was stirred for 3.5 hours at 0° C. Mono-BOC ethylenediamine was dissolved in 0.1 ml of dry methylene chloride and cooled to 0° C. Then this solution was added to the desethanolamine gramicidin mixture and the resulting mixture was stirred for an additional 30 min at 0° C. and then at room temperature for 8 hours. After concentrating to dryness, the BOC-protected gramicidamine was purified using preparative silica:chromatography (9:1 methylene chloride:methanol) eluent. ESI-MS shows a [M−H] fragment at 1979.66.

A mixture of 1 ml of 1:1 methylene chloride:trifluoroacetic acid, 0.1 ml dimethylsulfide and 0.02 ml ethanedithiol was prepared and cooled to 0° C. BOC-protected gramicidamine (2 mg, 1 µmol) was dissolved in the cooled mixture. The reaction was allowed to warm up to room temperature and stirred for 3 hours. The reaction mixture was concentrated down, dissolved in 9:1 DCM:MeOH and filtered. The filtrate was concentrated en vacuo and purified by silica chromatography using 9:2:0.1 DCM:MeOH:AcOH. The purified material was concentrated down en vacuo and taken up in 2 ml of 2:1 methylene chloride:methanol. The mixture was added dropwise to a stirring beaker of 100 ml of water. The resulting precipitate was collected by filtration. ESI-MS shows a [M+H]$^+$ fragment at 1881.62 and a retention time of 40.5 min by HPLC. Overall yield was 74% from desethanolamine gramicidin A.

Synthesis of gramicidazide (FIG. 6, structure 4): Gramicidamine (9 mg, 4.8 µmol) was dissolved in 1.2 ml MeOH and to this, a solution containing Na$_2$CO$_3$ (3 mg, 28.8 µmol) and CuSO$_4$.5H$_2$O (1 mg, 4 µmol) in water was added. A solution of trifyl azide in DCM was then added. The reaction was allowed to stir for 13 hours. The solution was concentrated en vacuo and purified by silica:chromatography (9:1 DCM: MeOH). The title compound was obtained at a 39% yield. ESI-MS showed a [M+Na]$^+$ fragment at 1929.93 and a [M−H]$^-$ at 1905.89. HPLC retention time is 42.1 min.

Synthesis of gA-triazole-benzenesulfonamide: Gramicidazide (1.5 mg, 0.79 µmol) and 4-carboxylbenzenesulfonamide N-propargyl amide (0.30 mg, 1.26 µmol) was dissolved in 0.1 ml of tert-butanol. To the solution of gramicidazide, a solution of sodium ascorbate (1.1 mg, 5.5 µmol) and CuSO$_4$.5H$_2$O (700 µg, 2.8 µmol) in water was added. The reaction was stirred for 3 days and a yield of 88% was obtained. ESI-MS showed a [M+2Na]$^{2+}$ fragment at 1095.41 and a [M−H]− at 2143.05 and the HPLC retention time was 37.6 min.

Synthesis of gA-NH-Gly-BOC: Gramicidamine (1.2 mg, 0.64 µmol), N-hydroxysuccinimidyl N'—BOC-glycine (0.52 mg, 2 µmol), and DIEA (0.32 µl, 2 µmol) were dissolved in 0.4 ml of THF. Reaction was stirred for 14 hours. Reaction mixture was purified by HPLC and a yield of 76% was obtained. HPLC retention time was 43.31 min and ESI-MS showed [M+2Na]$^{2+}$, [M+Na]$^+$, and [M−H]$^-$ fragments at 991.91, 2061,42 and 2037.36, respectively.

Synthesis of gA-NH-Benzenesulfonamide: Gramicidamine (1.2 mg, 0.64 µmol), N-hydroxysuccinimidyl 4-carboxylate benzenesulfonamide (0.57 mg, 2 µmol), and DIEA (0.32 µl, 2 µmol) were dissolved in 0.4 ml of THF. Reaction was stirred for 14 hours. ESI-MS showed [M+2Na]$^{2+}$, [M+Na]$^+$, and [M−H]$^-$ fragments at 1052.96, 2086.71 and 2062.12, respectively.

Synthesis of gramidicin-thiol (FIG. 6, structure 5): Desethanolamine gramicidin A (23 mg, 12.5 µmol) and triethylamine (7 µL, 50 µmol) were added to 0.4 ml of dry methylene chloride and the resulting mixture was stirred and cooled to 0° C. After adding ethyl chloroformate (5.4 µL, 50.8 µmol) to the cooled mixture, the reaction was stirred for 3.5 hours at 0° C. Cystineamine was dissolved in 0.25 ml in solvent containing 4:1 DCM:DMF. The mixture of cystineamine was added to the desethanolamine gramicidin solution and the resulting mixture was stirred for an additional 30 min at 0° C. and then at room temperature for 8 hours. The solution was concentrated en vacuo and the concentrate was dissolved in 1 ml of MeOH. DTT (15.4 mg, 100 µmol) was added and the reaction was allowed to stir at room temperature for 8 hours. The reaction mixture was concentrated down and taken up in 2 ml of 2:1 methylene chloride:methanol. The mixture was added dropwise to a stirring beaker of 100 ml of water. The resulting precipitate was collected by filtration and subjected to column chromatography using 9:1 DCM: MeOH. ESI-MS showed a [M+Na]$^+$ fragment at 1920.93 and a [M–H]$^-$ at 1895.67.

TABLE 3

Figure 6:
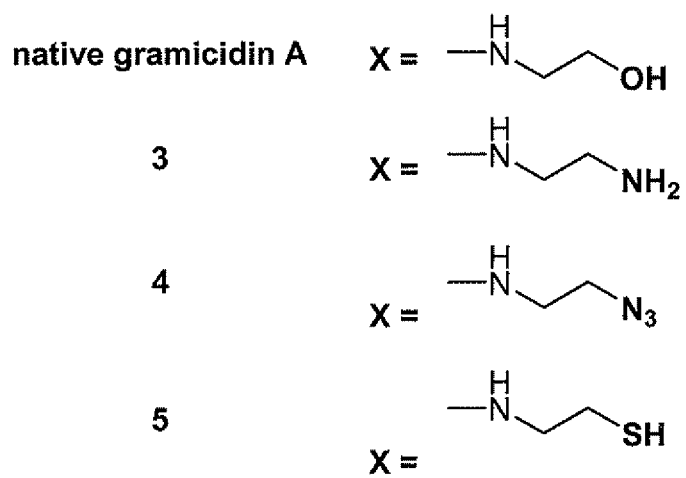
FIG. 6 provides sequences of native gramicidin A, gramicidamine (1), gramicidazide (2), and gramicidin thiol (3) as presented in FIGS. 7 and 8, Table 3, and the Novel reactive analogs of gramicidin A example.

Results of the Reactivity of gA analogs set forth in FIG. 6.

| substrate | | Solvent | % yield | % conversion |
|---|---|---|---|---|
| 3 | BOC-Gly-NHS | DCM | 67 | 83 |
| 3 | BOC-Gly-NHS | MeCN | 67 | 83 |
| 3 | BOC-Gly-NHS | DMF | 67 | 83 |
| 3 | BOC-Gly-NHS | MeOH | 65 | 82 |
| 3 | BOC-Gly-NHS | THF | 64 | 82 |
| 3 | Biotin-NHS | DCM | ? | ? |
| 3 | Sulfonamide-NHS | DCM | ~60 | ? |
| Native gA | BOC-Gly-NHS | DCM | 0 | 0 |
| Native gA | BOC-Gly-NHS | MeCN | 0 | 0 |
| Native gA | BOC-Gly-NHS | DMF | 0 | 0 |
| Native gA | BOC-Gly-NHS | MeOH | 0 | 0 |
| Native gA | BOC-Gly-NHS | THF | 6 | 6 |
| Native gA | Biotin-NHS | DCM | ? | ? |
| Native gA | Sulfonamide-NHS | DCM | ? | ? |
| 5 | Sulfonamide-maleimide | DCM | ? | ? |
| 4 | Sulfonamide-propargyl amide | MeOH | 88 | ? |

EXAMPLE 2

In this example a method to formally convert the C-terminal alcohol on gramicidin A (gA, 1, a natural ion channel forming peptide) to a reactive amine or azide functionality in order to make gA readily accessible for facile and selective synthesis of ion channel-based molecular probes is provided. The data demonstrates that these two gA-based building blocks, designated gramicidamine (2) and gramicidazide (3), are readily amenable to conventional synthetic derivatization to produce robust and active ion channels carrying tailored chemical functionality. Starting from these two building blocks, four additional, novel derivatives of gA are provided and characterized electrophysiologically on a single channel level. Also provided are exemplary uses of these reactive gA building blocks for development of ion channels that can be used for monitoring a "click" reaction, in situ, or for detecting a specific protein-ligand interaction in solution.

Figure 11:
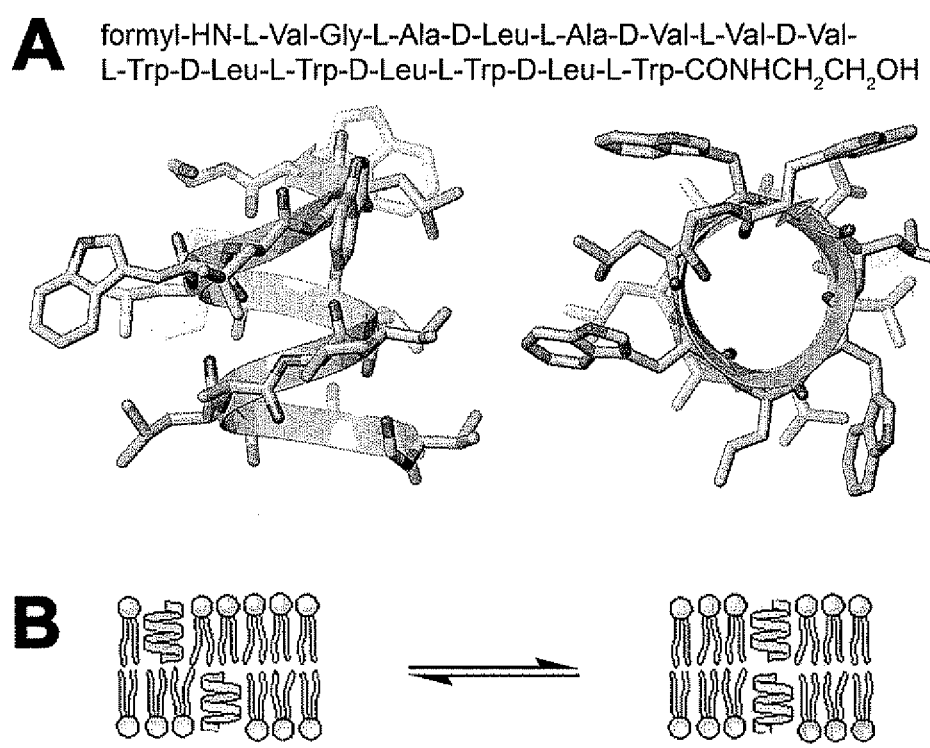
FIG. 11 depicts the amino acid sequence and structure of a monomer of gramicidin A (gA) (adapted from the crystal structure of gA, 1GRM) and the reversible dimeric assembly of a gA pore in a lipid bilayer. A) Sequence and helical structure (side view on the right and top view on the left) of gA. B) Pore formation of gA: the reversible dimerization of two gA molecules at their N-termini via hydrogen-bonding produces an open pore that spans the lipid bilayer and conducts monovalent cations.

FIG. 11 panel A shows the sequence and helical structure of gA. Gramicidin A reversibly dimerizes in a bilayer (FIG. 11 panel B), forming an N-terminus to N-terminus dimeric structure held together by a network of hydrogen bonds. The C-termini in these dimeric structures are exposed to the aqueous solutions on either side of a bilayer, and C-terminal modifications affect (but do not destroy) the conductance properties of the peptide.

Figure 9:
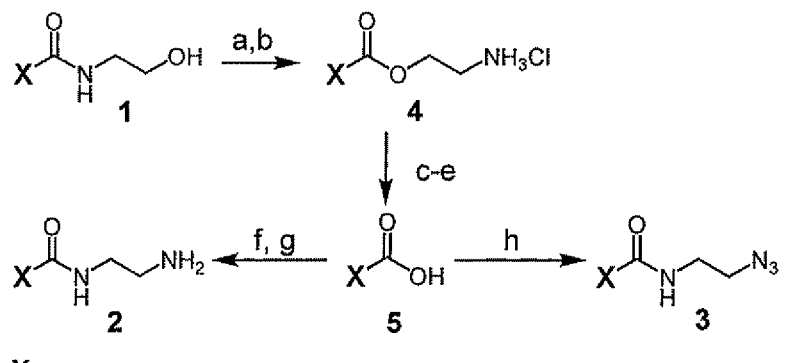
FIG. 9 depicts a scheme for the synthesis of gramicidamine (2) and gramicidazide (3). a) $POCl_3$, acetonitrile (ACN); b) $H_2O$, ACN (96% yield, 2 steps); c) acetic anhydride, formic acid, tertrahydrofuran (THF) (72% yield) d) LiOH, $H_2O$, THF; e) HCl, $H_2O$ (65% yield, 2 steps); f) $ClCO_2CH_2CH_3$ ($ClCO_2Et$), $N(CH_2CH_3)_3$ ($NEt_3$), dichloromethane (DCM) followed by N-tert-butyloxycarbonyl-ethylenediamine (N—BOC-ethylenediamine); g) trifluoroacetic acid (TFA), ethanedithiol (EDT), dimethyl sulfide ($Me_2S$), DCM (74% yield, 2 steps); h) $ClCO_2Et$, $NEt_3$, THF followed by 2-azido-ethylammonium chloride, $H_2O$, NaOH (69% yield). All yields correspond to isolated yields.
Figure 10:
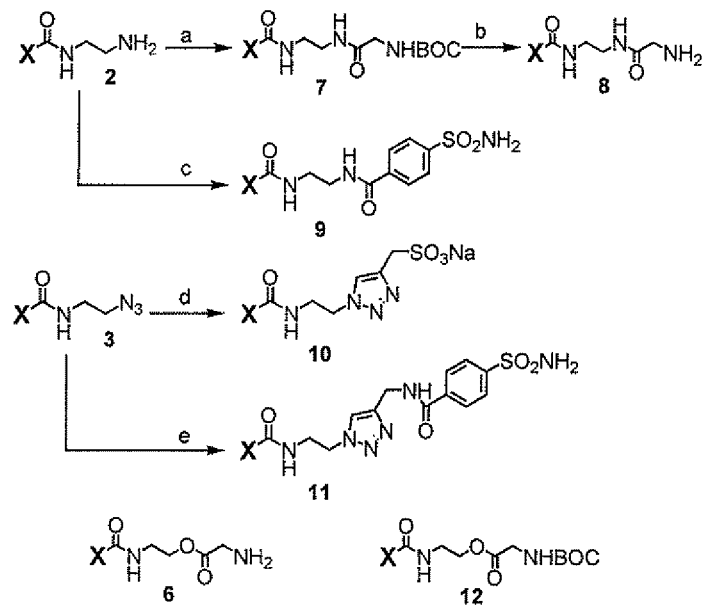
FIG. 10 depicts a scheme for the synthesis of gA derivatives from gA-based building blocks 2 and 3 and the structures of two ester derivatives of gA (6 and 12) derived from native gA. a) NHS ester of BOO-protected glycine, diisopropylethylamine (DIEA), THF; b) TFA, Me2S, EDT, DCM (62% yield over 2 steps); c) NHS ester of 4-sulfonamidobenzoate, DIEA, THF (41% yield); d) N-propargyl-4-sulfonamidobenzamide, $CuSO_4·5H_2O$, sodium ascorbate, $H_2O$, tert-butanol (t-BuOH) (88% yield); e) propargyl sulfonate, $CuSO_4·5H_2O$, sodium ascorbate, $H_2O$, t-BuOH (32%).

In order to develop an improved method to generate C-terminally modified derivatives of gA, a practical procedure to convert large quantities of native, commercial gA to gA-based building blocks carrying reactive C-terminal functional groups is provided. Accordingly, as shown in FIGS. 9 and 10, synthetic procedures for preparing gramicidamine (structure designated 2 in FIGS. 9 and 10) and gramicidazide (structure designated 3 in FIGS. 9 and 10) are provided. Gramicidamine and gramicidazide were used a building blocks to synthesize four novel derivatives of gA which were characterized functionally by single channel recordings. The data shows that gramicidamine and gramicidazide are more reactive than native gA towards desired chemical derivatization. The data also demonstrate an increased stability under conventional ion channel recording conditions of the amide and triazole groups generated from derivatization of gramicidamine and gramicidazide compared to previously reported ester linkages on gA.

To demonstrate the selective reactivity of the azide group in gramicidazide, a single channel recordings was used to monitor, in situ, a "click" reaction between gramicidazide and propargyl sulfonate under typical conditions for 1,3-dipolar cycloaddition reactions. In addition, an example of a biochemically-relevant sensing application of a molecule derived from gramicidazide that reports the interaction between a sulfonamide moiety and carbonic anhydrase is provided. Finally, the present data confirm the specificity of this protein-ligand interaction by competitive displacement of a gA derivative carrying a sulfonamide (see e.g., FIG. 10, structure 11) with 4-carboxybenzene sulfonamide.

To convert the C-terminal alcohol of native gA to an amine or azide functionality, a strategy that removed the entire C-terminal ethanolamine residue of gA to afford desethanolamine gA was instituted (see FIG. 9). To this end, native gA was reacted with excess POCl$_3$ to convert the C-terminal ethanolamine to a putative oxazoline intermediate, followed by treatment with H$_2$O in acetonitrile to afford the amino ester (FIG. 9, structure 4). To hydrolyze the ester in structure 4, the primary amine was reacted with a formyl group (to prevent it from converting rapidly back to gA under alkaline conditions), and hydrolyzed the ester group of this N-formyl derivative of structure 4 with LiOH to give desethanolamine gA (FIG. 9, structure 5). Finally, desethanolamine gA was reacted with N—BOC-ethylenediamine (followed by acidic deprotection of the BOC group) to afford the desired gramicidamine (FIG. 9, structure 2) or with azidoethylammonium chloride to afford the desired gramicidazide (FIG. 9, structure 3).

The chemical reactivity of gramicidamine and gramicidazide were examined. Their chemical reactivity was identified using a set of molecules that represent typical substrates for conjugation to amine or azide groups. For gramicidamine, the reactivity of the amine functionality was examined with molecules containing activated ester groups. FIG. 10 shows that gramicidamine reacts in good yield with the N-hydroxysuccinimidyl (NHS) ester of N-tert-butyloxycarbonyl-protected (BOC-protected) glycine and with the NHS ester of 4-sulfonamidobenzoate in the presence of diisopropylethylamine (as a base catalyst). It was also demonstrated in several organic solvents that these common amidation conditions afforded the expected products in good yield (see Table 4), suggesting that issues of substrate solubility, which are often problematic, should not limit the ability to synthesize desired gA derivatives. For comparison, it was demonstrated that native gA had little to no reactivity with the NHS ester of BOC-protected glycine in the presence of a base catalyst in a variety of organic solvents (Table 4).

TABLE 4

Summary of reactions of native gA (1), gramicidamine (2), and gramicidazide (3) with molecules that represent typical substrates for conjugation to amines and azides.

| compound[a] | substrate[b,c] | solvent | product | % yield[e] |
|---|---|---|---|---|
| 2 | BOC-Gly-NHS | DCM | 7 | 67 |
| 2 | BOC-Gly-NHS | MeCN | 7 | 67 |
| 2 | BOC-Gly-NHS | DMF | 7 | 67 |
| 2 | BOC-Gly-NHS | MeOH | 7 | 65 |
| 2 | BOC-Gly-NHS | THF | 7 | 64 |
| 1 | BOC-Gly-NHS | DCM | 12 | 0 |
| 1 | BOC-Gly-NHS | MeCN | 12 | 0 |
| 1 | BOC-Gly-NHS | DMF | 12 | 0 |
| 1 | BOC-Gly-NHS | MeOH | 12 | 0 |
| 1 | BOC-Gly-NHS | THF | 12 | 0 |
| 2 | NHS 4-sulfonamido-benzoate | THF | 9 | 73 |
| 3 | propargyl sulfonate | $H_2O$ + t-BuOH[d] | 10 | 32 |
| 3 | N-propargyl-4-sulfamoyl-benzamide | $H_2O$ + t-BuOH[d] | 11 | 88 |

[a] The concentration of structure 1 and 2 was 1.6 mM in all cases. The concentration of 3 was 1.7 mM when reacted with sodium propargyl sulfonate and 2.6 mM when reacted with N-propargyl-4-sulfamoylbenzamide.
[b] All reactions with 1 and 2 contained 1.5 equivalents (eq) of diisopropylethylamine (DIEA) and 2 eq of the NHS ester. The reaction between 3 and sodium propargyl sulfonate contained 8 eq of sodium ascorbate, 3 eq of $CuSO_4 \cdot 5H_2O$, and 1.6 eq of sodium propargyl sulfonate. The reaction between 3 and N-propargyl-4-sulfamoylbenzamide contained 7 eq of sodium ascorbate, 3.5 eq of $CuSO_4 \cdot 5H_2O$, and 1.6 eq of N-propargyl-4-sulfamoylbenzamide.
[c] NHS = N-hydroxysuccinimidyl.
[d] The solvent was a 2:1 mixture of t-BuOH:$H_2O$.
[e] Yields were determined by HPLC.

To confirm the stability of ester derivatives of gA, gramicidyl glycine (FIG. 10, structure 6) was synthesized and tested for stability in acidic (pH 3.5) and in basic solutions (pH 10.4). In acidic solutions, hydrolysis of the ester moiety of gramicidyl glycine was not observed after 24 hours at 23° C. Hydrolysis of the ester of gramicidyl glycine was observed after 3 hours at 23° C. in the basic solution (as determined by HPLC analysis). For comparison, structure 8, which was prepared using the method presented here and hence contained an amide linkage between the gramicidamine and a glycine group (FIG. 10) as opposed to the ester in gramicidyl glycine, was stable toward hydrolysis under acidic (pH 3.4) and basic (pH 10.4) conditions over a period of 24 hours at 23° C. These results highlight two important advantages of molecules derived from gramicidamine: First, the synthetic route to molecules derived from gramicidamine is simplified and proceeds in reasonable yield compared to molecules derived from native gA, and second, the stability of molecules derived from gramicidamine in aqueous solutions extends the range of applications of ion channel-based probes compared to ion channels generated through direct esterification of native gA.

In addition to synthesizing gramicidamine for direct comparison of reactivity and stability with gA, gramicidazide was synthesized containing an azide group that is expected to have orthogonal reactivity to the C-terminal alcohol in native gA or the C-terminal amine in gramicidamine. Since organic azides undergo 1,3-dipolar cycloaddition reactions with terminal alkynes under mild conditions in water, we tested the reactivity of gramicidazide with propargyl sulfonate and N-propargyl-4-sulfamoylbenzamide as representatives of typical, terminal alkyne substrates (Scheme 2). As expected, reaction of gramicidazide with these two alkyne substrates in the presence of $Cu^I$ as metal catalyst afforded triazole cycloaddition structure 10 and 11 in modest to good yield (Table 4).

Figure 12:
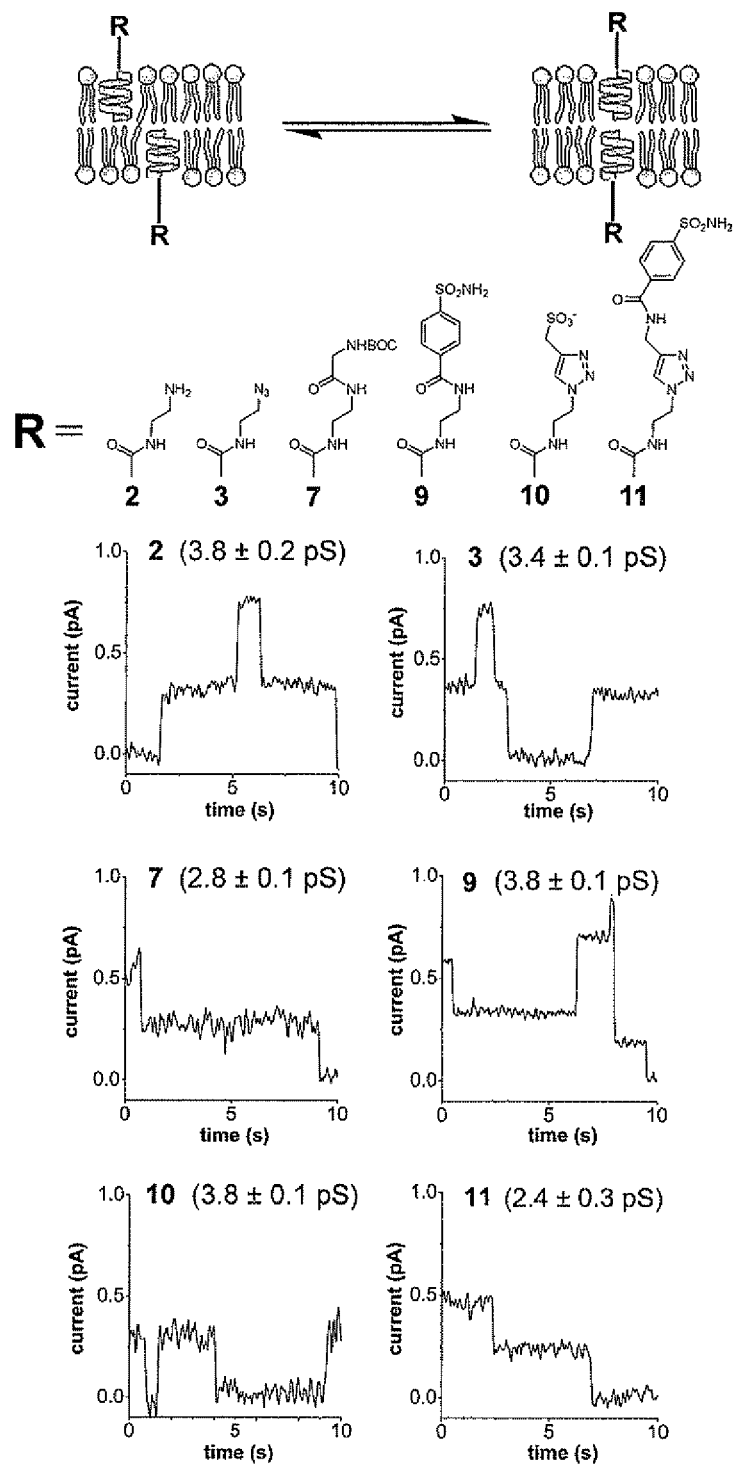
FIG. 12 depicts the reversible dimerization of six different derivatives of gA and original single channel traces of current versus time of all six derivatives. The applied potential was 100 mV and the electrolyte solution contained 20 mM KCl and 0.2 mM HEPES (pH 7.4) in all experiments. The conductance values (listed on top of every current trace) were determined from the slopes of current versus voltage (I-V) curves. Complete analysis of traces over long periods of time showed occasional subconductance. Conductance values are mean values determined from linear best fits of the I-V curves of the main conductance states in the linear range from −75 mV to +75 mV. All current traces were filtered with an analog filter with a cutoff frequency of 3 kHz followed by filtering with a digital Gaussian filter with a cutoff frequency of 4 Hz.

The single channel conductance of various products (e.g., structures 2, 3, 7, and 9-11) was measured in planar lipid bilayers in order to demonstrate that molecules derived from gramicidamine and gramicidazide retained their activity as functional ion channels. FIG. 12 shows representative single channel traces of current versus time of these gA derivatives under an applied potential of 100 mV. These current recordings illustrate that gramicidamine and gramicidazide, as well as derivatives generated from gramicidamine and gramicidazide, all retained well-defined ion channel activity.

Figure 13:
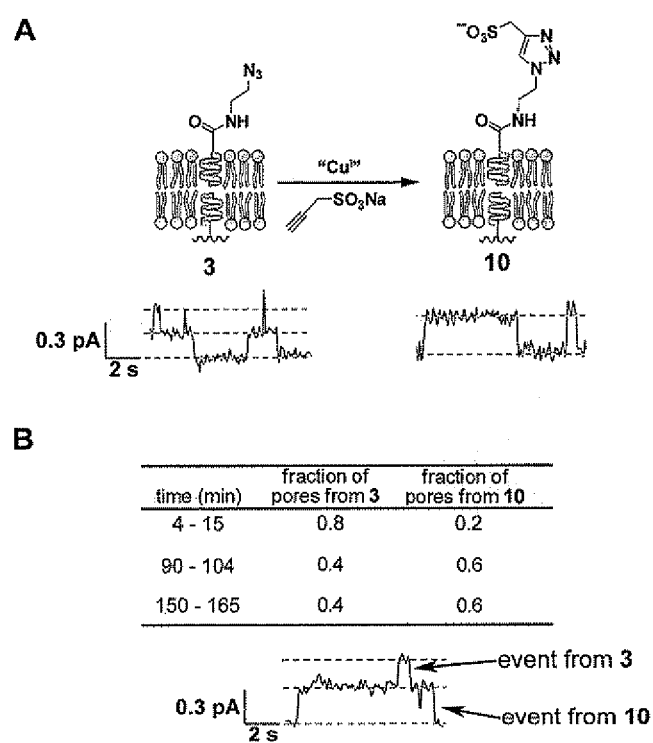
FIG. 13 depicts the conversion of gramicidazide 3 to a negatively charged triazole sulfonate 10. A) ion channels comprised of 3 and 10 in a membrane and their corresponding single ion channel conductance traces. The single channel conductance of 10 (4.3±0.1 pS) is larger than the single channel conductance of 3 (3.3±0.1pS) when measured in low ionic strength recording media. B) The table indicates the fraction of observed ion channel events that correspond to the starting material (gramicidazide 3) and the product of the reaction (triazole sulfonate 10) over time windows between 4-15, 90-104, and 150-165 minutes throughout the course of the reaction. The current versus time trace in B shows a time window during the course of the reaction where an ion channel event from 3 occurs at the same time as an ion channel event from 10. All current versus time traces were generated at an applied voltage of +75 mV in recording media containing 20 mM KCl, 0.2 mM HEPES (pH 7.4), 2 mM sodium ascorbate, 2 mM propargyl sulfonate, and 0.5 mM $CuSO4$. The pH of the solution was 6.9. The initial concentration of 3 was 40 pMi.

"Click" reactions were monitored in situ using single ion channel recordings. Conductance measurements were used to identify the reactivity of the azide group of gramicidazide towards reaction with terminal alkynes in the presence of a $Cu^I$ atalyst and to demonstrate the capability to follow the course of this chemical reaction on individual pores. Single ion channel conductance measurements were used to monitor, in situ, the conversion of the azide group in gramicidazide to a negatively-charged triazole cycloaddition product (FIG. 13, structure 10). Measurement of the conductance of pure samples of structure 10 and gramicidazide confirmed that derivatives of gA carrying a negative charge near the opening of the pore increased conductance compared to neutrally charged derivatives of gA. A single channel conductance ($\gamma$) of 4.3±0.1 pS for structure 10 and 3.3±0.1 pS for gramicidazide was obtained under the recording conditions used to monitor the cycloaddition reaction shown in FIG. 13. The difference in conductance between gramicidazide and a negatively-charged triazole cycloaddition product may be used to estimate the relative conversion of starting material gramicidazide to product (negatively-charged triazole cycloaddition product) throughout the course of the reaction (FIG. 13).

Gramicidazide was added to a final concentration of 40 pM to both 4 mL chambers of a stirred lipid bilayer setup comprised of zwitterionic 1,2-diphytanoyl-sn-glycero-3-phosphatidylcholine (DiPhyPC) lipids that separated two compartments containing 20 mM KCl, 0.2 mM HEPES buffer, 2 mM sodium ascorbate (as a reducing agent for $Cu^{II}$), and 2 mM propargyl sulfonate. The final pH of this solution was 6.9. $CuSO_4$ was added (to give a final concentration of $Cu^{II}$ of 0.5 mM) to both chambers of the bilayer setup and recorded the single ion channel activity over time. Although the substrate and catalyst were added to both chambers of the bilayer setup, it is noted that only changes in the chemical properties of molecules attached near the entrance of the pore (and not the exit of the pore) affect the conductance through gA-based ion channels. The cycloaddition reaction was monitored at a constant applied potential of +75 mV. Accordingly, these experiments confirmed that the chemical reactions on gramicidazide are occurring on the positively polarized side of the membrane (which represents the entrance of the pore). The table in FIG. 13 summarizes the results from ion channel conductance measurements throughout the course of this reaction. The conductance values from ion channel events were analyzed in a time window from the 4th to 15th minute after the start of the reaction, it was observed that approximately 20% of the ion channel events corresponded to an ion channel with conductance value significantly higher that gramicidazide, which we attribute to the presence of structure 10. Measurement of ion channel events over a window of time between 90-104 minutes of incubation revealed that the reaction between gramicidazide and propargyl sulfonate had proceeded to give approximately 60% product. Analysis of the channel events from the reaction mixture between 150-165 minutes showed the same ratio of structure 10 to starting material gramicidazide as observed between the time window of 90-104 minutes, suggesting the reaction was complete after ~90 minutes. These results illustrate the utility of tailored gA derivatives for monitoring the progress of synthetic reactions using single ion channel conductance measurements.

Figure 14:
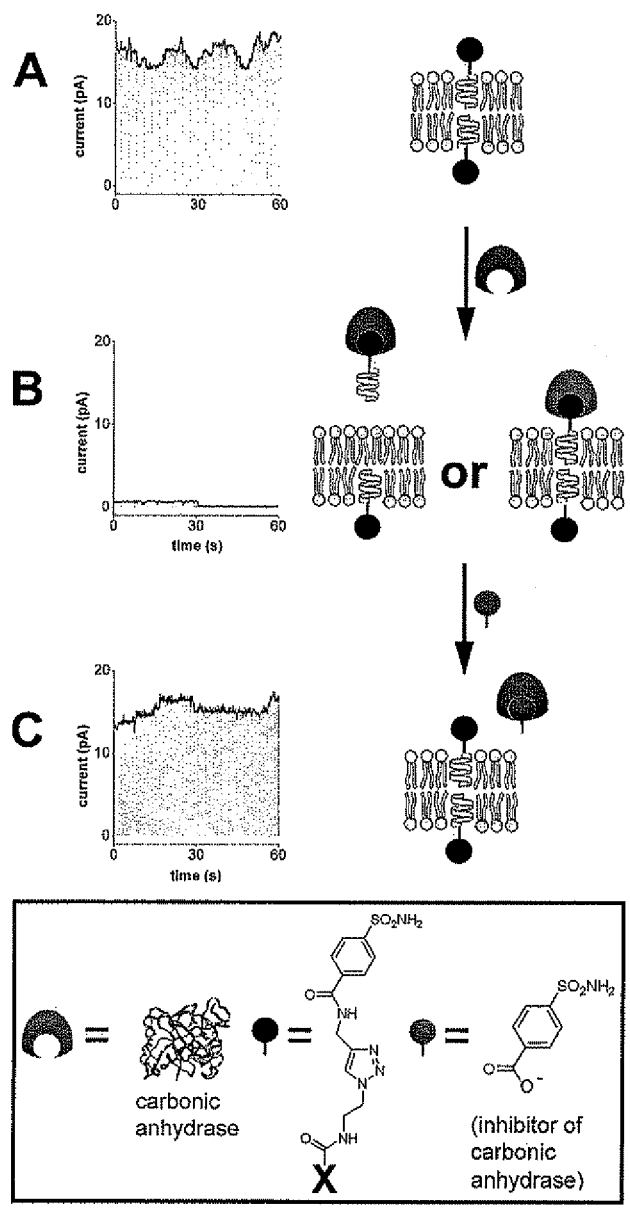
FIG. 14 depicts the detection of carbonic anhydrase (CA) with gA derivative 11. A) two molecules of 11 that dimerize to form an open pore across a membrane are shown. The accompanying current versus time trace shows the conductance of multiple, simultaneous opening events in the membrane. B) Binding of gA-sulfonamide 11 by CA reduces the observed transmembrane ion flux through 11. C) Addition of a competitive inhibitor of CA (4-carboxybenzenesulfonamide) restored ion channel activity and hence demonstrated specificity of binding of 11 to CA. The recording electrolyte contained 140 mM KCl and 10 mM phosphate buffer (pH 8.0). The current traces were recorded at 100 mV. X=HCO-Val-Gly-Ala-Leu-Ala-Val-Val-Val-Trp-Leu-Trp-Leu-Trp-Leu-Trp-.

Also provided herein are ion channel-based sensors for detection of protein-ligand interactions. In order to illustrate the synthetic utility of gA-based building blocks gramicidamine and gramicidazide for construction of ion channel-based sensors, the detection of a protein-ligand interaction using ion channel recordings was obtained. FIG. 10 shows that molecules gramicidamine and gramicidazide can be used to synthesize gA derivatives such as structure 9 and structure 11, which both carry benzenesulfonamide moieties. Benzenesulfonamides are well-known ligands for carbonic anhydrase II (CA, EC 4.2.1.1), a $Zn^{2+}$-containing protein. The present studies further show that a derivative of gA carrying a benzenesulfonamide group may be used to detect the presence of CA in solution. The data demonstrates that gramicidazide makes it possible to expand the scope of biological interactions that can be explored using ion channel measurements by focusing on a protein-ligand interaction with a binding constant that is typically found in biology $K_d=10^{-6}-10^{-9}$ M) such as the association of CA with a benzenesulfonamide ligand. FIG. 14, panel A, shows the conductance of multiple, simultaneous openings of pores of structure 11 (at a concentration of 12 pM) in a bilayer made from DiPhyPC lipids. Upon addition of CA to one side of the bilayer to give a final concentration of CA of 50 µM, suppression of ion channel activity was observed (FIG. 14, panel B). The $K_d$ for binding of benzenesulfonamides to CA can range from $10^{-6}-10^{-9}$ M. A significant fraction of structure 11 may be associated with CA at these concentrations of protein and gA derivative. Two potential mechanisms can explain the decrease in observed channel activity upon binding of CA to structure 11:1) CA may have associated with structure 11 and cause the CA-bound structure 11 to partition less in the membrane compared to structure 11 alone (i.e., binding of CA may have extracted structure 11 from the bilayer), or 2) CA may have associated with membrane-bound structure 11 and sterically blocked ions from entering or exiting the channel (FIG. 14, panel B). Both mechanisms would result in the observed strong reduction in channel activity and they may act in parallel.

Excess of a competitive inhibitor, 4-carboxybenzene sulfonamide, was added to the aqueous solution to displace structure 11 from CA. Upon addition of the competitive inhibitor, a rapid restoration (within 20 seconds) of ion channel activity was observed (FIG. 14, panel C), confirming the specificity of the interaction between CA and structure 11. These results illustrate the utility of gA-based building blocks gramicidamine and gramicidazide for the identification of protein-ligand interactions in membranes as well as for sensing applications.

Synthesis of 2-aminoethyl gramicidate (FIG. 9, structure 4): Gramicidin A (142 mg, 75 µmol) was added to 10 mL of acetonitrile (ACM). Phosphorus oxychloride (287 µL, 3 mmol) was added dropwise to the solution of gA and the reaction was stirred at 23° C. for 4 hours. The reaction mixture was concentrated to dryness and 10 mL of a 4:1 mixture of CAN:H₂O was added. The mixture was stirred for 20 minutes, concentrated to dryness and dissolved in 5 mL of a 2:1 mixture of dichloromethane (DCM):methanol (MeOH). This mixture was added dropwise to a stirred beaker containing 200 mL of H₂O. The resulting precipitate was collected by filtration. The crude yield was 96% by weight. The retention time by HPLC was 34.7 min. ESI-MS (m/z) calculated for $C_{99}H_{140}N_{20}O_{17}$ (M⁺), 1882.07; found (M–H)⁻, 1880.85.

Synthesis of N-formyl-2-aminoethyl gramicidate: Anhydrous formic acid (0.55 mL, 14.4 mmol) was combined with acetic anhydride (1.36 mL, 14.4 mmol) and heated to 65° C. for 30 minutes. After cooling the formic acid/acetic anhydride solution to 23° C., the mixture was added to 2-aminoethyl gramicidate 4 (139 mg, 72 µmol) that was dissolved in 20 mL of dry tetrahydrofuran (THF). The reaction was stirred for 3.5 hours followed by concentration to dryness. We dissolved the crude product in a minimal volume of a 2:1 mixture of DCM:MeOH at 23° C. (until the solution was clear) and added this solution dropwise to a stirred beaker containing 200 mL of H₂O. The resulting precipitate was collected by filtration and taken to the next step without further purification. When performing these reactions on smaller scales (<100 mg of peptides), it is possible to isolate the product by silica chromatography using DCM:MeOH (9:1) as the eluent to afford N-formyl-2-aminoethyl gramicidate as a white powder in 72% isolated yield. ESI-MS (m/z) calculated for $C_{100}H_{140}N_{20}O_{18}$ (M⁺), 1910.07; found (M+Na)⁺, 1932.97.

Synthesis of desethanolamine gA (FIG. 9, structure 5): The crude product of N-formyl-2-aminoethyl gramicidate (150 mg, 78 µmol) was dissolved in 25 mL of THF. In a separate flask, LiOH.H₂O (327 mg, 7.8 mmol) was dissolved in 25 mL of H₂O. The two mixtures were combined and stirred at 23° C. for 3 hours, followed by slow addition of 1 M HCl until the solution had a pH of 2. The reaction mixture was concentrated en vacuo to dryness and redissolved in 15 mL of 2:1 DCM:MeOH. The mixture was added dropwise to 150 mL of H₂O while stirring. The resulting precipitate was collected by filtration and purified by silica chromatography. The eluent initially consisted of a mixture of CHCl₃:MeOH:H₂O:acetic acid (750:75:10:2.5) to elute the less-polar impurities. After confirming by thin layer chromatography (TLC) that the impurities had eluted, the eluent was changed to CHCl₃:MeOH:H₂O:acetic acid (200:30:4:1). The fractions containing desethanolamine gA 5 were concentrated en vacuo, and the resulting gel was re-dissolved in 15 mL of 2:1 DCM:MeOH. The mixture was added dropwise to 150 mL of H₂O while stirring. The resulting precipitate was collected by filtration to yield 93 mg of 5 (65% yield over two steps from 4). ESI-MS (m/z) calculated for $C_{97}H_{135}N_{19}O_{17}$ (M)⁺, 1839.03; found (M+Na)⁺, 1861.94. The retention time by HPLC was 40.7 minutes.

Synthesis of gramicidamine (FIGS. 9 and 10, structure 2): Desethanolamine gA (structure 5) (25 mg, 13.6 µmol) and triethylamine (7.6 µL, 54.4 µmol) were added to 1 mL of anhydrous THF and the resulting mixture was stirred and cooled to 0° C. After adding ethyl chloroformate (5.20 µL, 54.4 µmol) to the cooled mixture, the reaction was stirred for 3.5 hours at 0° C. Mono-tert-butyloxycarbonyl (BOC) ethylenediamine, (8.6 µL, 54.4 µmol, purchased from Alfa Aesar), was dissolved in 0.2 mL of THF and cooled to 0° C. This solution was added to the mixture containing desethanolamine gA and the resulting solution was stirred for an additional 30 minutes at 0° C., followed by stirring at 23° C. for 8 hours. After concentrating to dryness, the BOC-protected gramicidamine was purified using preparative silica chromatography (using a 9:1 mixture of DCM:MeOH as eluent). ESI-MS (m/z) calculated for $C_{104}H_{149}N_{21}O_{18}$ (M⁺), 1981.14; found (M–H)⁻, 1979.66.

A mixture containing 1 mL of DCM, 1 mL of trifluoroacetic acid (TFA), 0.1 mL of dimethylsulfide, and 0.05 mL of ethanedithiol was prepared and cooled to 0° C. BOC-protected gramicidamine (22.4 mg, 11.3 µmol) was dissolved in the cooled mixture. The reaction was allowed to warm up to 23° C. and stirred for 3 hours. The reaction mixture was concentrated en vacuo to dryness and purified by silica chromatography. The eluent initially consisted of a mixture of DCM:MeOH (9:1) to elute the less-polar impurities. After confirming by thin layer chromatography (TLC) that the impurities had eluted, the eluent was changed to DCM: MeOH (9:2). HR-MS (m/z) calculated for $C_{99}H_{141}N_{21}O_{16}$ (M+H)+, 1881.0937; found (M+H)+, 1881.0943. The retention time by HPLC was 40.5 minutes. The overall yield was 74% (19 mg) from desethanolamine gA.

Synthesis of structure 7 (see FIG. 10): Gramicidamine (1.2 mg, 0.64 μmol), (N—BOC-protected) glycine N-hydroxysuccinimidyl ester (0.52 mg, 2 μmol), and diisopropylethylamine (DIEA, 0.32 μL, 2 μmol) were dissolved in 0.4 mL of THF. The reaction was stirred for 14 hours at 23° C. The product was purified by HPLC. The isolated yield of 7 was 76%. The retention time by HPLC was 43.3 minutes. HR-MS (m/z) calculated for $C_{106}H_{152}N_{22}O_{19}S$ (M+H)+, 2038.1676; found (M+H)+, 2038.1661.

Synthesis of structure 9 (see FIG. 10): Gramicidamine (1.2 mg, 0.64 mmol), 4-carboxybenzenesulfonamide N-hydroxysuccinimidyl ester (0.57 mg, 2 μmol), and DIEA (0.32 μL, 2 μmol) were dissolved in 0.4 mL of THF. The reaction was stirred for 14 hours at 23° C. The product was purified by HPLC. The isolated yield of structure 9 was 41%. The retention time by HPLC was 37.6 minutes. HR-MS (m/z) calculated for $C_{106}H_{146}N_{22}O_{19}S$ (M+H)+-, 2064.0928; found (M+H)+, 2064.1015.

Synthesis of sodium propargyl sulfonate: Propargyl bromide (1 mL, 9 mmol), purchased from Acros Organics as a solution containing 80 wt % in toluene, and sodium sulfite (1.43 g, 11.35 mmol) were dissolved in 3.5 mL of $H_2O$ and 3.5 mL of MeOH. The mixture was stirred for 7 hours at 65° C. MeOH (60 mL) was added and the resulting precipitate was filtered and removed. The filtrate was diluted in acetone and the resulting precipitate was collected as white crystals (1.3 g, 81% yield). ESI-MS (m/z) calculated for $C_3H_3O_3S$ (M)+, 118.98; found (M)+, 119.04. $^1$H-NMR ($D_2O$, 400 MHz): δ 3.849 (d, 2H, 1.4 Hz), 2.714 (t, 1H, 1.4 Hz).

Synthesis of 2-azidoethylammonium chloride: Sodium azide (236 mg, 3.6 mmol) and 2-bromoethylammonium bromide (200 mg, 0.98 mmol) were dissolved in 1 mL of $H_2O$. The reaction was refluxed at 95° C. for 1 hour. After cooling the solution to 23° C., 1 M NaOH was added to the solution until the pH was 12. The 2-azidoethylammonium chloride was then co-distilled with $H_2O$, acidified to pH 4 with 1 M HCl, and lyophilized to provide 76 mg of product as a white powder (65% yield). ESI-MS (m/z) calculated for $C_2H_6N_4$ (M)+, 86.06; found (M+H)+, 86.99. $^1$H-NMR ($D_2O$, 400 MHz): δ 3.414 (t, 2H, 5.6 Hz), 3.301 (t, 2H, 5.6 Hz).

Synthesis of gramicidazide (FIG. 9, structure 3): Desethanolamine gA (20 mg, 10.8 μmol) and DIEA (7.6 μL, 43.4 μmol) were added to 2 mL of anhydrous THF and the resulting mixture was stirred and cooled to 0° C. After adding ethyl chloroformate (4.6 μL, 43.4 μmol) to the cooled mixture, the reaction was stirred for 3.5 hours at 0° C. Separately, 2-azidoethylammonium chloride (5.3 mg, 43.4 μmol) was dissolved in 0.2 mL of 1 M NaOH and cooled to 0° C. This solution was added to the mixture containing desethanolamine gA and the resulting solution was stirred for an additional 30 minutes at 0° C. and then at 23° C. for 8 hours. After concentrating to dryness, the product was purified using preparative silica chromatography (using a mixture of 9:1 DCM: MeOH as eluent) to give 14.2 mg of gramicidazide (69% yield). HR-MS (m/z) calculated for $C_{99}H_{139}N_{23}O_{16}$ (M+H)+, 1907.0842; found (M+H)+, 1907.0782. The retention time by HPLC was 42.4 minutes.

Synthesis of structure 10 (FIG. 10): Gramicidazide (10 mg, 5.2 μmol) and sodium propargyl sulfonate (1.2 mg, 8.6 μmol) were dissolved in 2 mL of tert-butanol (t-BuOH). Sodium ascorbate (8.2 mg, 41.4 μmol) was dissolved in 0.5 mL of $H_2O$, and $CuSO_4.5H_2O$ (2.6 mg, 10.4 μmol) was dissolved separately in 0.5 mL of $H_2O$. The solution of sodium ascorbate was added to the solution of gramicidazide 3, followed by addition of the solution of $CuSO_4.5H_2O$. The reaction was stirred at 23° C. for 14 hours. The solution was then concentrated on vacuo and purified by HPLC to give 32% yield of structure 10. The retention time by HPLC was 36.1 minutes. HR-MS (m/z) calculated for $C_{102}H_{143}N_{23}O_{19}S$ (M–H)−, 2025.0578; found (M–H)−, 2025.0512.

Synthesis of N-propargyl-4-sulfamoylbenzamide: Propargyl amine (34 μL, 0.497 mmol) and 4-carboxybenzenesulfonamide (100 mg, 0.497 mmol) were dissolved in 2 mL of dry dimethylformamide. N-hydroxybenzotriazole (44.7 mg, 0.33 mmol), 0-(benzotriazol-1-yl)-N,N,N',N'-tetramethyluronium hexafluorophosphate (188 mg, 0.497 mmol) and DIEA (79.4 μL, 0.497 mmol) were added in this order to the stirred solution. After 4 hours, the solution was evaporated to dryness and 30 mL of ethylacetate was added. The solution was washed twice with 30 mL of $H_2O$ and with 30 mL of brine, dried over $Na_2SO_4$, filtered, and concentrated to dryness. The compound was purified by column chromatography using a 1:4 mixture of DCM:ethylacetate as eluent, affording 52 mg (44% yield) as a white solid. $^1$H-NMR (DMSO-$d_6$, 400 MHz): δ 9.148 (t, 1H, 5.6 Hz), 8.003 (d, 2H, 8.4 Hz), 7.902 (d, 2H, 8.4 Hz), 7.506 (s, 2H), 4.075 (m, 2H), 3.172 (t, 1H, 2.4 Hz).

Synthesis of structure 11 (FIG. 10): Gramicidazide (1.5 mg, 0.79 μmol) and N-propargyl-4-sulfamoylbenzamide (0.30 mg, 1.26 μmol) was dissolved in 0.2 mL of t-BuOH. To the solution of gramicidazide, a solution of sodium ascorbate (1.1 mg, 5.5 μmol) dissolved in 0.05 mL of $H_2O$ was added, followed by addition of a solution of $CuSO_4.5H_2O$ (700 μg, 2.8 μmol) dissolved in 0.05 mL of $H_2O$. The reaction was stirred for 3 days. The solution was then concentrated en vacuo and purified by HPLC to give an 88% yield of structure 11. HR-MS (m/z) calculated for $C_{109}H_{149}N_{25}O_{19}S$ (M+H)+, 2145.1254; found (M+H)+, 2145.1216. The retention time by HPLC was 37.6 minutes.

Formation of Planar Lipid Bilayers: Planar lipid bilayers were formed by the "folding technique." Briefly, a film (e.g., Teflon®, Eastern Scientific Inc, pore diameter 0.1-0.2 mm) that was pretreated on both sides of the pore with 2 μL of 5% (v/v) hexadecane in pentane. This film was mounted using vacuum grease (Dow Corning, High vacuum grease) to a custom-made Teflon chamber separating two buffer compartments each with a volume capacity of 4 mL. After addition of 1 mL of electrolyte (20 mM KCl buffered with 0.2 mM HEPES pH 7.4 or 140 mM KCl buffered with 10 mM phosphate pH 8.0) to each compartment, lipids were spread at the air-water interface of the electrolyte solution in both compartments. Three additional milliliters of the same electrolyte solution were added to each compartment to raise the liquid level above the aperture in the Teflon film. The bilayers were formed on the pore of the Teflon film by aspirating the electrolyte solution into a 3 mL syringe, followed by dispensing the electrolyte solution back into each compartment. This cycle of raising and lowering the liquid levels was repeated until a bilayer was obtained that had a minimum capacitance of 70 pF and that was stable (i.e., no significant current fluctuations above the baseline noise level) at 100 mV of applied potential for at least 2 minutes.

Ion Channel Measurements: Single channel recordings in "voltage clamp mode" were performed using Ag/AgCl pellet electrodes (Warner Instruments) in each compartment of the bilayer setup. Data acquisition and storage was carried out using custom software in combination with an EPC-7 patch clamp amplifier from Heka (set at a gain of 10 mV pA$^{-1}$ and a filter cutoff frequency of 3 kHz). The data acquisition board for the amplifier was set to a sampling frequency of 15 kHz. All current traces shown in the figures were further filtered using a digital Gaussian low-pass filter with a cutoff frequency of 4 Hz.

The analysis of single channel current traces was performed by computing histograms of the currents from the original current versus time traces with ClampFit 9.2 software from Axon Instruments. From these histograms, main current values were extracted by fitting a Gaussian function to the peaks in the histograms. All gramicidin molecules showed a predominant conductance and occasionally subconductance states (i.e., single channel currents that were smaller than the main current values). Single channel conductances reported in this paper always refer to the main conductance state (i.e., to the dominant peaks in the current histograms). All conductance values were obtained from the slopes of current versus voltage (I-V) curves taken at −75, −50, +50 and +75 mV.

Monitoring a 1,3-dipolar cycloaddition ("click") reaction in situ using single ion channel recordings: About 3 µl, (from a 100 ng mL$^{-1}$ solution in ethanol) of gramicidazide was added (to afford a final concentration of 40 pM of gramicidazide) to each compartment of a bilayer setup containing as electrolyte 20 mM KCl and 0.2 mM HEPES buffer. Solutions of sodium ascorbate and sodium propargylsulfonate were added to both compartments to bring the final concentration of each molecule to 2 mM. A solution of $CuSO_4.5H_2O$ was added to each compartment to a final concentration of 0.5 mM. The final pH of this solution was 6.9. In order to facilitate the analysis of single ion channel traces, the concentration of gramicidazide was kept low (40 pM) during the reaction to minimize the possibility for multichannel events (i.e., opening of two or more channels simultaneously). This strategy made it possible to observe measured currents that would frequently return to baseline (i.e., current steps separated by no observed channel events). Consequently, a small number of events over time were observed, and thus analyzed the data over a window of time rather than at specific time points. Events were recorded over time windows of 4-15, 90-104 and 150-165 minutes throughout the course of the reaction. The percent composition of gramicidazide and structure 10 in the reaction mixture in each time window were estimated by manually counting the number of observed single ion channel events corresponding to the conductance of gramicidazide or structure 10. For the 4-15 minute time window, we measured 26 total channel events. For the 90-105 and 150-165 minute time windows, we recorded 15 total channel events. Since the number of total channel events from each time window was limited to 15-26 events, the reported percent of conversion of starting material to product are estimated values. The capacitance of the folded membranes throughout the course of these studies ranged from 70-88 pF. The conductivities of the buffer before and after the reaction were 323 and 336 mS cm$^{-1}$, respectively.

Detection of protein-ligand binding interactions using ion channel measurements: About 1 µL (from a 100 ng mL$^{-1}$ solution in ethanol) of structure 11 (to afford a final concentration of 12 pM of structure 11) was added to each compartment of a bilayer setup containing as electrolyte 140 mM KCl and 10 mM phosphate buffer (pH 8.0). The conductance was recorded at 100 mV. Upon addition of bovine carbonic anhydrase II (CA, EC 4.2.1.1) to the trans compartment to bring the final concentration of CA to 50 µM, the membrane broke and was refolded. We recorded the conductance through the refolded membrane for 40 minutes to assure that the observed reduction of ion channel activity was due to the interaction of CA with structure 11. We then added 4-carboxybenzenesulfonamide (to give a final concentration of 1.5 mM of inhibitor) to the trans compartment of the bilayer setup, and again observed that the membrane broke during this addition. After refolding the membrane, we rapidly observed (within 20 seconds of re-establishing a planar lipid bilayer) the re-emergence of significant ion channel activity. The capacitance of all folded membranes throughout the course of these studies ranged from 84-88 pF.

EXAMPLE 3

The following example provides an ion channel platform for detecting the activity of enzymes through their reaction with tailored substrates attached to gramicidin A (gA) or derivatives thereof. The platform provided herein exploits the catalytic activity of an enzyme in combination with the amplification characteristics of ion conductance through an ion channel-forming peptide (gA) to detect picomolar concentrations of an analyte (e.g., an active protein) in aqueous solution.

The activity of enzymes can be indicative of normal or abnormal cellular function, and can be used to diagnose diseases. Here, we investigate alkaline phosphatase (AP) as a model enzyme to explore the possibility of employing an ion channel platform (FIG. 15) as a novel analytical strategy for detecting enzyme activity. Assessing AP activity in blood is a routine part of health examinations since abnormal levels can be early indicators of cancer or liver damage. Accordingly, also provided herein are methods of an ion channel-based strategy for the detection of enzymatic activity that offers at least four complementary advantages compared to current platforms. These advantages include: (1) the method utilizes the amplification characteristics of ion flux through a single ion channel to achieve high sensitivity; (2) the method is orthogonal to colorimetric assays and can, therefore, be advantageous for solutions that are strongly colored or contain quenchers of fluorescence or intrinsic fluorescence (e.g., blood); (3) the method requires very small quantities (<1 picomole) of the ion channel probe (which minimizes cost); and (4) the nanoscale size of ion channels provides for the development of enzyme activity assays within miniaturized, cost-effective, and potentially portable devices.

As noted throughout the specification, single ion channel recordings can be used to detect, in situ, the reactivity of molecules in solution. The detection is based on the chemical modification of the charge on functional groups near the opening of a gA pore. This type of detection is also designated "charge-based sensing. The charged group presented at a bilayer surface may cause a significant change in the local concentration of ions. This change in local ion concentration may, in turn, affect the conductance of ion channels that are embedded in a bilayer. The present platform and methods utilize this change in single channel conductance to detect a reaction that modifies the charge on substrates attached to the entrance of an ion pore.

In an exemplary embodiment, a charge-based sensing platform may be used to detect the enzyme activity of AP through its capability to catalyze the hydrolysis of negatively-charged phosphate groups on substrates attached to the C-terminus of gA or derivatives thereof. The data provided herein demonstrate that enzymatic hydrolysis of a phosphate group from gA and the concomitant removal of two negative charges from the entrance of the gA pore results in a measurable change in single channel conductance, representing the first example of the detection of enzyme activity by monitoring changes in single ion channel conductance through an ion channel.

Figure 16:
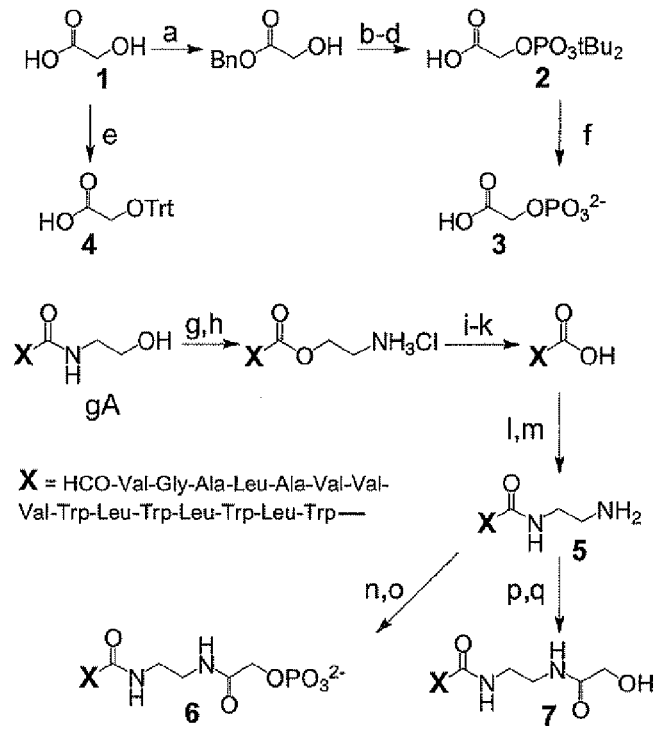
FIG. 16 depicts the synthesis of alkaline phosphatase substrates 3 and 6 and their respective hydrolysis products 1 and 7. a) Benzyl bromide, acetone, triethylamine ($NEt_3$), 60° C. (51% yield); b) di-tert-butyl-N,N-diethyl phosphoramidite, tetrazole, dry tertrahydrofuran (THF); c) m-chloro perbenzoic acid, warmed from −78° C. to 23° C.; d) $H_2$, Pd/C, methanol (40% yield over 3 steps); e) trityl chloride, diisopropylethylamine (DIEA), dichloromethane (DCM) (22% yield); f) trifluoroacetic acid (TFA), DCM (91% yield); g) $POCl_3$, acetonitrile (ACN); h) $H_2O$, ACN (96% yield over 2 steps); i) acetic anhydride, formic acid, THF (72% yield); j) LiOH, $H_2O$, THF; k) HCl., $H_2O$ (65% yield, over 2 steps); l) $ClCO_2Et$, $NEt_3$, DCM followed by N-tert-butyloxycarbonyl ethylenediamine; m) TFA, ethane dithiol (EDT), dimethyl sulfide ($Me_2S$), DCM (74% yield over 2 steps); n) molecule 2, 2-ethoxy-1-ethoxycarbonyl-1,2-dihydroquinoline (EEDQ), $NEt_3$, DCM; o) TFA, EDT, $Me_2S$, DCM (58% yield over 2 steps); p) molecule 4, EEDQ, DIEA, THF; q) TFA, EDT, $Me_2S$, DCM (72% yield over 2 steps). Bn=benzyl, tBu=tert-butyl, Trt=trityl.

A substrate for alkaline phosphatase (AP) was attached to the opening of a gA pore. The substrate included glycolic acid-O-phosphate (FIG. 16, structure 3). As attached to the C-terminus of gA (see FIG. 16), it presents a negatively charged phosphate group proximal to the opening of the pore. As confirmed by $^{31}$P-NMR spectroscopy, a substrate including glycolic acid-O-phosphate was hydrolyzed by AP.

Figure 15:
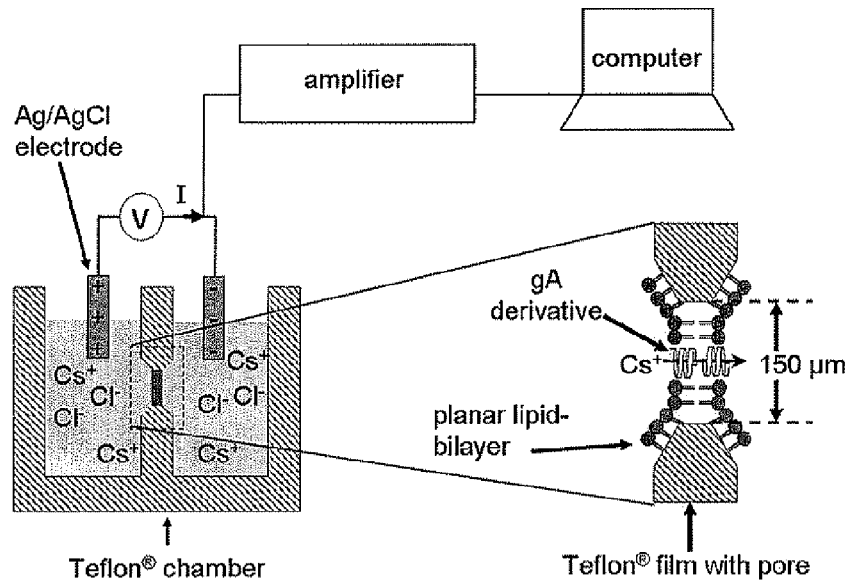
FIG. 15 depicts a planar lipid bilayer platform for recording single ion channel currents through an ionophore such as derivatives of gramicidin A. The chamber includes two compartments filled with a recording electrolyte containing e.g., CsCl as a source of monovalent cation. The aqueous compartments are separated by a film that supports a planar lipid bilayer. Each compartment contains one Ag/AgCl electrode that is submerged in the recording electrolyte. When a voltage is applied by a patch clamp amplifier, cesium cations pass through pores formed by two molecules of a gA derivative (embedded in the bilayer) and creates a measurable current. A computer may be used to store and analyze the recorded currents.
Figure 17:
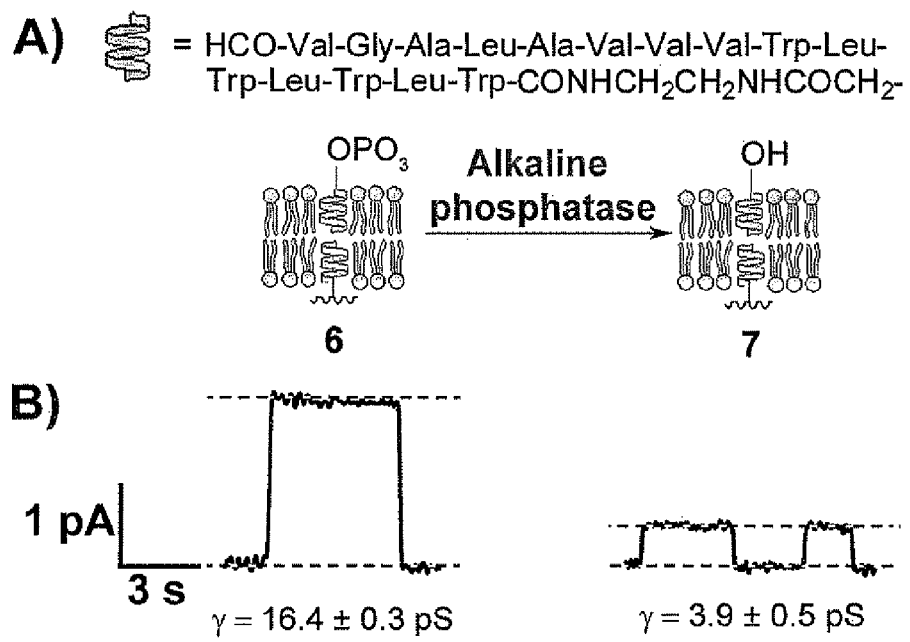
FIG. 17 depicts the detection of alkaline phosphatase (AP) activity using an ion channel platform. A) Conversion of a negatively-charged phosphate group on gA derivative 6 to a neutral alcohol in the presence of AP. B) Representative single ion channel recordings of 6 and 7. These original current-versus-time traces were recorded using as electrolyte a buffered solution containing 50 mM CsCl, 1 mM $MgCl_2$ and 0.5 mM $K_2CO_3$ at pH 9.8. The applied potential was +125 mV.
Figure 20:
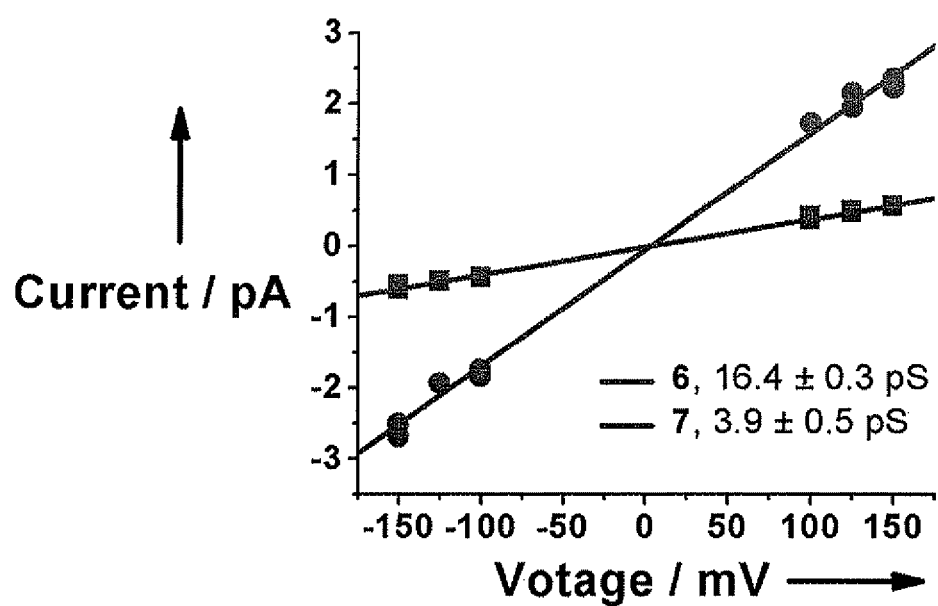
FIG. 20 depicts current versus voltage (I-V) curves from single channel currents. The phosphorylated derivative (solid circles), exhibited a larger conductance than the de-phosphorylated analog (solid squares). The slopes from the linear fits of these I-V curves provided an estimate of the conductance of phosphorylated derivative (16.4±0.3 pS) and de-phosphorylated derivative (3.9±0.5 pS). These I-V curves were recorded using as electrolyte a buffered solution containing 50 mM CsCl, 1 mM $MgCl_2$ and 0.5 mM $K_2CO_3$ at pH 9.8.

The single channel conductance of gA phosphate (FIG. 16, structure 6) and its hydrolysis product (FIG. 16, structure 7) was measured by incorporating them into a planar lipid bilayer setup (FIG. 15). FIG. 17 shows representative current-versus-time traces of gA phosphate and its hydrolysis product under an applied potential of 125 mV in buffered recording electrolyte. gA phosphate exhibiting a larger (by a factor of 4) conductance than the gA phosphate hydrolysis product. The difference may be related to the pre-concentration of cesium cations near the negatively charged phosphate group presented at opening of the ion channel pore in 6. Analysis of the current-versus-voltage (I-V) curves of 6 and 7 revealed distinct single channel conductance values ($\gamma$) of 16.4±0.3 pS for 6 and 3.9±0.5 pS for 7 in this recording electrolyte (see FIG. 20). These results indicate that the conversion of gA derivative 6 to 7 can be used for detection of the de-phosphorylating enzyme activity of AP by employing single ion channel conductance measurements.

As is known to the skilled artisan, alkaline phosphatase dephosphorylates a target substrate, e.g., the charged substrate becomes more "neutral" resulting in a decrease in ion flow through the ionophore associated with the target substrate. This change or modulation of ion flow is detectable by a platform provided herein. Also contemplated herein are platforms whereby a neutral or uncharged substrate associated with an ionophore becomes "charged" by the addition of a chemical group such as a phosphate. In this example, the ion flow through the ionophore would increase. Similar to a decrease in ion flow, an increase in ion flow is also detectable by a platform provided herein. Exemplary substrates would include substrates that can be phosphorylated by an enzyme such as a kinase. Accordingly, a change in ion flow or "ion flux" can be detected as an increase or decrease in flow through an ionophore.

It is understood that any substrate-enzyme interaction that alters the charge at the opening of an ionophore can be used in the present platform and methods.

To detect a change in single ion channel currents, gA phosphate was added to a final concentration of about 200 pM to both compartments of a planar lipid bilayer platform (FIG. 15) containing a recording electrolyte. AP was added to a final concentration of about 600 nM and the enzymatic conversion of gA phosphate to its hydrolysis product over time was monitored. We estimated the time-dependent conversion of gA phosphate to its hydrolysis product by comparing the fraction of events from gA phosphate to the fraction of events from its hydrolysis product throughout the course of the reaction. The fraction of ion channel events from the hydrolysis product was defined as the number of events originating from the hydrolysis product ($\gamma \approx 4$ pS) divided by the total number of events (from gA phosphate and hydrolysis product) observed during a 5 or 10 min interval of recording. Similarly, the fraction of ion channel events from gA phosphate was defined as the total number of events originating from gA phosphate ($\gamma \approx 16$ pS) divided by the total number of events observed during a 5 or 10 min interval of recording.

Figure 18:
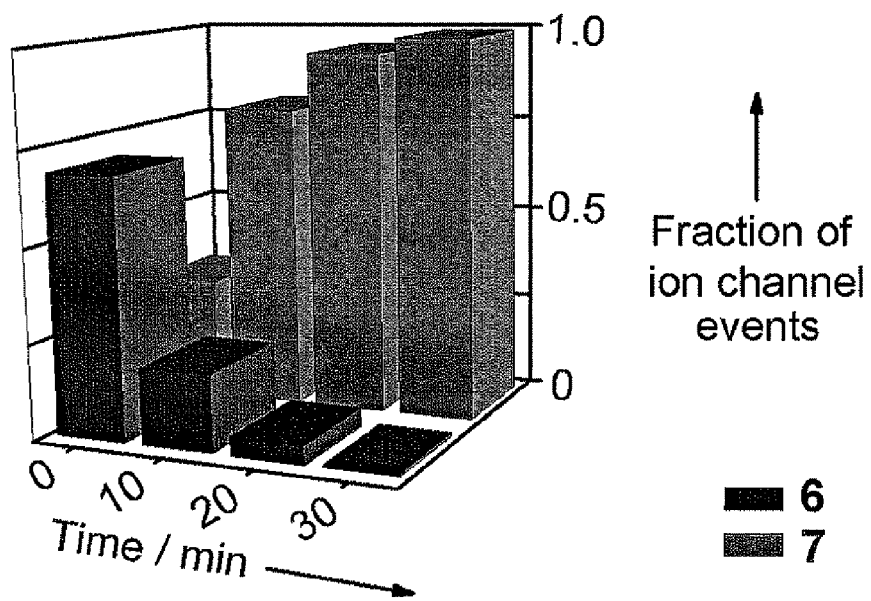
FIG. 18 depicts the time dependent enzymatic hydrolysis of the phosphate group in 6 to 7 in the presence of 600 nM AP as determined using single ion channel conductance measurements. The fraction of total ion channel events corresponding to 6 or 7 were estimated over time by counting the number of big ($\gamma \approx 16$ pS) and small ($\gamma \approx 4$ pS) events within 5 minute time intervals; these intervals were separated by 10 min.
Figure 19:
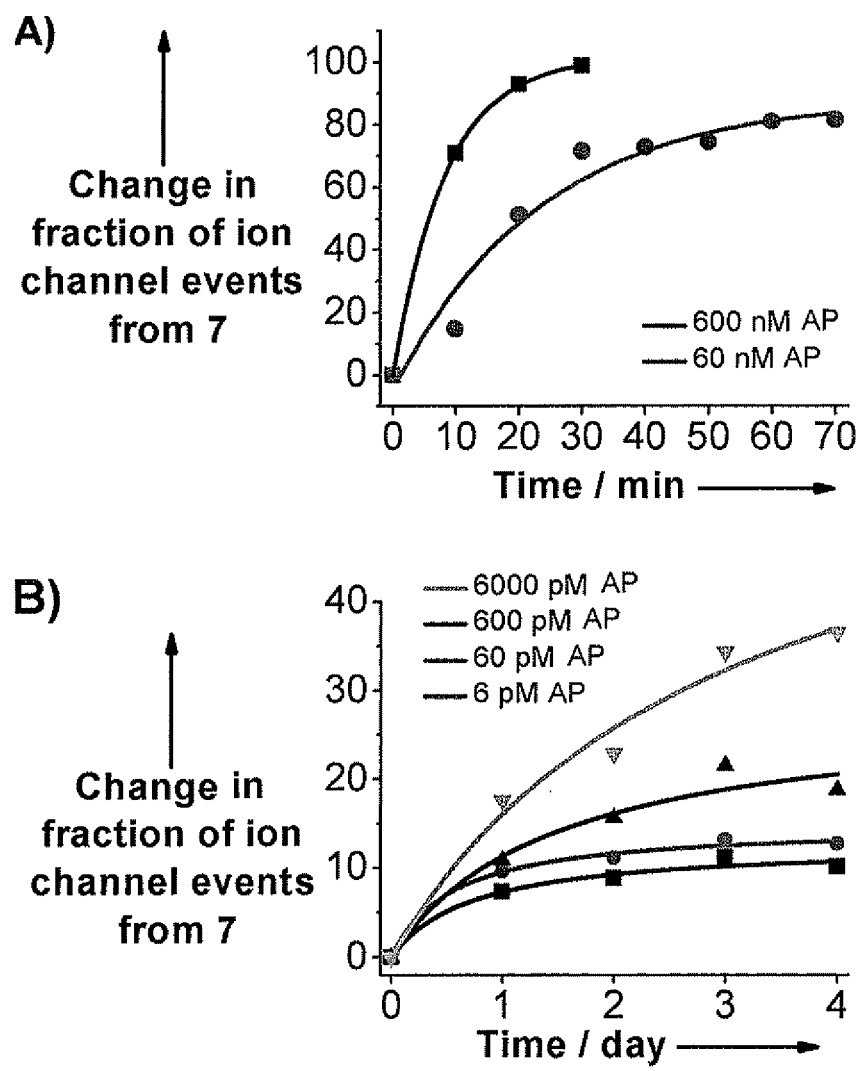
FIG. 19 depicts the formation of 7 from enzymatic hydrolysis of 6 over time as a function of the concentration of AP using single ion channel conductance measurements. A) In situ detection of the hydrolysis of 200 pM 6 in the presence of 60 nM and 600 nM AP. B) Ex situ detection of the hydrolysis of 6 to 7 over 4 days. Solutions containing 120 pM gA derivative 6 were incubated with 6 pM-6 nM AP in vials (outside of the bilayer chamber) at 23° C. Reaction progression was monitored in daily intervals by introducing aliquots of the reaction mixture to the planar lipid bilayer setup. Before addition of AP, ion channel recordings showed that a fraction of events (<30%) corresponded to impurities of the hydrolysis product (7) in the samples of gA phosphate (6). The data is represented as the change in the fraction of events that we recorded from gA derivative 7 with respect to the fraction of events from 7 before addition of AP (i.e., all data points are shown relative to the background in the absence of AP).

FIG. 18 shows that while the enzymatic reaction progressed in the bilayer chamber, the fraction of ion channel events from gA phosphate decreased whereas the fraction of events from the hydrolysis product increased. FIG. 18 also illustrates that after 35 min almost all recorded ion channel events originated from the hydrolysis product. No hydrolysis was observed in the ion channel experiments over the course of 1 h in the absence of AP. FIG. 19, panel A, shows that in situ measurements of ion channel events provide for the monitoring of the hydrolysis of gA phosphate to the hydrolysis product by AP at enzyme concentrations as low as 60 nM. Bilayer experiments may be limited to ~1 h due to the limited stability of the bilayer membrane. In order to afford extended reaction times that would make it possible to explore the detection limit of the assay, samples of gA phosphate were incubated with solutions of AP at concentrations ranging from 6 pM to 6 nM in reaction vials (i.e., outside of the bilayer setup) for 4 days prior to daily analysis of single ion channel events. FIG. 19, panel B, shows that this ex situ incubation strategy made it possible to detect picomolar concentrations of AP corresponding to femtomoles of enzyme in the bilayer chamber.

In general, the results shown in FIG. 19 demonstrate that an ion channel platform based on gA can be used to detect the activity of an enzyme in solution. This detection modality takes advantage of two fold amplification (the catalytic turn-over properties of enzymes and the amplification characteristics of ion flux through a single ion channel pore) to detect enzyme activity with high sensitivity.

Although the results described here demonstrate that ion channels can be employed to detect femtomoles of AP using a conventional bilayer setup, increasingly available automated, microfabricated (Schmidt et al., Angew. Chem. Int. Ed. 2000, 39, 3137-3140; Fertig et al., Biophys. J. 2002, 82, 3056-3062; Jeon et al., J. Am. Chem. Soc 2006, 128, 42-43; Malmstadt et al., Nano Lett. 2006, 6, 1961-1965; Shim et al., Anal. Chem. 2007, 79, 2207-2213; Uram et al., Angew. Chem. Int. Ed. 2006, 45, 2281-2285; Mach et al., Anal. Bioanal. Chem. 2008, 390, 841-846; Kreir et al., Lab Chip 2008, 8, 587-595) and chip-based (Laiwalla et al., Circuits and Systems I: Regular Papers, IEEE Transactions on [Circuits and Systems I: Fundamental Theory and Applications, IEEE Transactions on] 2006, 53, 2364-2370; Mayer et al., Biophys. J. 2003, 85, 2684-2695; Schmidt et al., Angew. Chem. Int. Ed. 2000, 39, 3137-3140; Sondermann et al., Biochim. Biophys. Acta 2006, 1758, 545-551) bilayer platforms can improve the stability of membranes as well as reduce the volume of electrolyte solutions required for single ion channel measurements. Such technological advances allow for the detection limit of ion channel platforms to sub-femtomole quantities of active enzymes in solution. Accordingly, the platforms provided herein may be automated such that ion channel recordings are accessible to a broad community by overcoming the requirement for specialized expertise. In addition, the platform and methods provided herein allow for the detection of a wide range of enzymes (such as disease-specific phosphatases and kinases by designing ion channels whose conductance behavior can be altered by the interaction of biologically or medically relevant enzymes with tailored ion channel pores. Due to its nanoscale size and single molecule detection characteristics, the ion channel-based strategy provided in this application is particularly well-suited for detecting enzyme activity within small volumes (such as, for instance, detecting kinase activity within individual cells).

Formation of Planar Lipid Bilayers: Planar lipid bilayers were formed by the "folding technique" as previously described. The recording electrolyte was 1 mM $MgCl_2$, 50 mM CsCl buffered with 0.5 mM $K_2CO_3$ at pH 9.8. Briefly, we spread a solution containing 25 mg mL$^{-1}$ 1,2-diphytanoyl-sn-glycero-3-phosphatidylcholine (DiPhyPC) lipids in pentane at the air-water interface of the electrolyte solution in both compartments of the bilayer setup. 3 mL of the total volume of 4 mL of electrolyte solution in each bilayer compartment was aspirated into a syringe, followed by dispensing the electrolyte solution back into each compartment. This cycle of raising and lowering the liquid levels was repeated until a bilayer was obtained that had a minimum capacitance of 70 pF and that was stable (i.e., no significant current fluctuations above the baseline noise level) at 100 mV of applied potential for at least 2 min.

Ion Channel Measurements: We performed single channel recordings in "voltage clamp mode" using Ag/AgCl pellet electrodes (Warner Instruments) in each compartment of the bilayer setup. Data acquisition and storage was carried out using custom software in combination with an EPC-7 patch clamp amplifier from Heka (set at a gain of 10 mV pA-1 and a filter cutoff frequency of 3 kHz). The data acquisition board (National Instruments, Austin, Tx) for the amplifier was set to a sampling frequency of 15 kHz. The current traces shown in the FIG. 2 were further filtered using a digital Gaussian low-pass filter with a cutoff frequency of 4 Hz.

Analysis of the single channel current traces was performed by computing histograms of the currents from the original current versus time traces with ClampFit 9.2 software from Axon Instruments. From these histograms we extracted the main current values by fitting a Gaussian function to the peaks in the histograms. All conductance values were obtained from the slopes of I-V curves.

Procedure for monitoring the enzymatic hydrolysis of 6 in the presence of AP using single ion channel recordings: For in situ measurements, about 19 µL (from a 100 ng mL-l solution in ethanol) of gA phosphate (to afford a final concentration of 200 pM of 6) was added to each compartment of a bilayer setup containing recording electrolyte. A solution of AP was added to both compartments. Ion channel events were recorded continuously over the course of the reaction. For ex situ experiments, AP was added (to a final concentration of 6 pM-6 nM) and gA phosphate (to a final concentration of 120 pM) to recording buffer that contained 2 µM BSA to stabilize AP at low concentrations. Single ion channel events were recorded during a 10 min time window once a day (50-250 events) over the course of 4 days by filling both compartments of the bilayer setup with 4 mL of the solutions with the desired AP concentration. The fraction of ion channel events from gA phosphate hydrolysis product was estimated in the reaction mixture at each time point by counting the number of observed single ion channel events corresponding to the conductance of gA phosphate and hydrolysis product within 5 min (for in situ measurements) or within 10 min (for ex situ measurements) time windows. The capacitance of the folded membranes throughout the course of these studies ranged from 79-81 pF.

Synthesis of benzyl glycolate: Glycolic acid (200 mg, 2.6 mmol) and triethylamine (401 µL, 2.86 mmol) were dissolved in 2.6 mL of acetone. After a couple minutes of stirring, benzyl bromide (279 µL, 2.34 mmol) was added to the solution. The reaction was refluxed at 60° C. for 12 h. The solution was filtered to remove precipitated triethylammonium bromide and was concentrated en vacuo. Purification was done by silica chromatography with dichloromethane (DCM) to remove the non-polar impurities and then 2% ethyl acetate (EtOAc) in DCM to elute the desired product as a colorless oil (200 mg, 51% yield). $^1$H-NMR (400 MHz, CDCl$_3$) δ 7.362 (5H, s) δ 5.198 (2H, s) δ 4.201 (2H, s) δ 3.366 (1H, s) ppm.

Synthesis of glycolic acid-O-(di-tert-butyl) phosphate (FIG. 16, structure 2): Di-tert-butyl-N,N-diethyl phosphoramidite (0.62 mL, 2.5 mmol), benzyl glycolate (265 mg, 1.6 mmol) and tetrazole (560 mg, 8 mmol) were dissolved in 46 mL of anhydrous tetrahydrofuran (THF). The reaction was stirred at 23° C. for 2 h and then it was cooled to −78° C. m-Chloro perbenzoic acid (825 mg, 4.8 mmol) was added to the cooled solution and was allowed to stir for 20 min at −78° C. and then warmed to 23° C. for 10 min. The solution was concentrated en vacuo and the crude material was dissolved in 30 mL of DCM and washed twice with 40 mL of saturated NaHCO$_3$, dried over Na$_2$SO$_4$ and concentrated en vacuo. The resulting crude oil was purified by preparative silica chromatography using DCM:acetone (9:1) to afford 240 mg of yellow oil. The compound was dissolved in 1.5 mL of methanol (MeOH) and subjected to 1 atm hydrogen over 240 mg Pd/C for 3 h. After filtration over celite, the filtrate was concentrated en vacuo to yield a pure colorless liquid (180 mg, 40% yield). $^1$H-NMR (300 MHz, CD$_3$OD) δ 4.477 (2H, d, J=9 Hz), δ 1.408 (18H, s); $^{31}$P-NMR (300 MHz, CD$_3$OD) δ-10.437 ppm using an internal $^{31}$P-NMR standard of 85% phosphoric acid.

Synthesis of glycolic acid-O-phosphate (FIG. 16, structure 3): Glycolic acid-O-(di-tert-butyl)phosphate, (6 mg, 22 µmol) was added to a 1.5 mL solution of 1:1 DCM:trifluoroacetic acid (TFA) and the resulting mixture was stirred at 23° C. for 3 h. The resulting solution was concentrated to dryness to yield a clear film of product (3.1 mg, 91% yield). $^1$H-NMR (300 MHz, CD$_3$OD) δ 4.477 (2H, d, J=9 Hz); $^{31}$P-NMR (300 MHz, CD$_3$OD) δ 3.33 ppm using an internal $^{31}$P-NMR standard for 85% phosphoric acid.

Synthesis of O-trityl-glycolic acid (FIG. 16, structure 4: A solution of glycolic acid (800 mg, 10.5 mmol) and of diisopropylethylamine (DIEA, 2.75 g, 9.9 mmol) was prepared in 5 mL of DCM. The resulting mixture was cooled to 0° C. A solution of trityl chloride (1.62 g, 37.6 mmol) in DCM was added dropwise to the cooled solution of glycolic acid and DIEA. The reaction was allowed to stir for 1 h at 0° C., then 18 h at 23° C. The solution was concentrated en vacuo. The reaction mixture was purified by silica chromatography using DCM as the eluent until all of the unreacted trityl chloride eluted. The polarity of eluent was increased to 45:4 (DCM/MeOH) to elute O-trityl glycolic acid. Upon concentration en vacuo, a white solid (902 mg, 22% yield) of O-trityl glycolic acid was obtained. $^1$H-NMR (400 MHz, CDCl$_3$): δ 3.89 (2H, s), δ 7.27-7.36 (9H, m), δ 7.47 (6H d, 8 Hz).

Synthesis of desethanolamine gA: Gramicidin A (142 mg, 75 µmol) was added to 10 mL of acetonitrile (ACN). Phosphorus oxychloride (287 µL, 3 mmol) was added dropwise to the solution of gA and the reaction was stirred at 23° C. for 4 h. The reaction mixture was concentrated to dryness and 10 mL of a 4:1 mixture of ACN:H$_2$O was added. The mixture was stirred for 20 min, concentrated to dryness and dissolved in 5 mL of a 2:1 mixture of DCM:MeOH. This mixture was added dropwise to a stirred beaker containing 200 mL of H$_2$O. The resulting precipitate of 2-aminoethyl gramicidate was collected by filtration. The crude yield was 96% by weight. The retention time by HPLC was 34.7 min. ESI-MS (m/z) calculated for C$_{99}$H$_{140}$N$_{20}$O$_{17}$ (M$^+$), 1882.07; found (M−H)$^-$, 1880.85.

Anhydrous formic acid (0.55 mL, 14.4 mmol) was combined with acetic anhydride (1.36 mL, 14.4 mmol) and heated to 65° C. for 30 min. After cooling the formic acid/acetic anhydride solution to 23° C., the mixture was added to 2-aminoethyl gramicidate (139 mg, 72 µmol) that was dissolved in 20 mL of dry THF. The reaction was stirred for 3.5 h followed by concentration to dryness. We dissolved the crude product in a minimal volume of a 2:1 mixture of DCM:MeOH at 23° C. (until the solution was clear) and added this solution dropwise to a stirred beaker containing 200 mL of $H_2O$. The resulting precipitate of N-formyl-2-aminoethyl gramicidate was collected by filtration. The product was isolated by silica chromatography using DCM:MeOH (9:1) as the eluent to afford N-formyl-2-aminoethyl gramicidate as a white powder in 72% isolated yield. ESI-MS (m/z) calculated for $C_{100}H_{140}N_{20}O_{18}$ (M+), 1910.07; found (M+Na)+, 1932.97.

N-formyl-2-aminoethyl gramicidate (150 mg, 78 µmol) was dissolved in 25 mL of THF. In a separate flask, $LiOH.H_2O$ (327 mg, 7.8 mmol) was dissolved in 25 mL of $H_2O$. The two mixtures were combined and stirred at 23° C. for 3 h, followed by slow addition of 1 M HCl until the solution had a pH of 2. The reaction mixture was concentrated en vacuo to dryness and redissolved in 15 mL of 2:1 DCM:MeOH. The mixture was added dropwise to 150 mL of $H_2O$ while stirring. The resulting precipitate was collected by filtration and purified by silica chromatography. The eluent initially consisted of a mixture of $CHCl_3$:MeOH:$H_2O$:acetic acid (750:75:10:2.5) to elute the less-polar impurities. After confirming by thin layer chromatography (TLC) that the impurities had eluted, the eluent was changed to $CHCl_3$:MeOH:$H_2O$:acetic acid (200:30:4:1). The fractions containing desethanolamine gA were concentrated en vacuo, and the resulting gel was re-dissolved in 15 mL of 2:1 DCM:MeOH. The mixture was added dropwise to 150 mL of $H_2O$ while stirring. The resulting precipitate was collected by filtration to yield 93 mg of desethanolamine gA (65% yield over two steps from 2-aminoethyl gramicidate). ESI-MS (m/z) calculated for $C_{97}H_{135}N_{19}O_{37}$ (M)+, 1839.03; found $(M_+Na)^+$, 1861.94. The retention time by HPLC was 40.7 min.

Synthesis of structure gramicidine A (gA) phosphate (FIG. 16, structure 6). O-(di-t-butylphosphate) glycolic acid, (3.4 mg, 12.6 µmol) and gramicidamine, (8 mg, 4.2 µmol) were dissolved in 2 mL of DCM. Triethylamine (0.72 µL, 15.1 µmol) was added to the solution. After 5 min, 2-ethoxy-1-ethoxycarbonyl-1,2-dihydroquinoline (EEDQ) (3.1 mg, 1.6 mmol) was added and stirring for 16 h at 23° C. The solution was concentrated and the resulting product was purified using preparative silica chromatography using as eluent a mixture of DCM:MeOH (9:1) to afford 6 mg of a yellow powder. A mixture of 1 mL of 1:1 DCM:TFA, 0.1 mL dimethylsulfide and 0.02 mL ethanedithiol was prepared and cooled to 0° C. The yellow powder was dissolved in this cooled mixture. The reaction was allowed to warm up to 23° C. and stirred for an additional 3 h. The reaction mixture was concentrated and charged with 2 mL of 2:1 DCM:MeOH. The mixture was added dropwise to a beaker of 100 mL of water while stirring. The resulting precipitate was collected by filtration as a yellow solid (5.6 mg, 58% yield). For conductance measurements, the compound was further purified by analytical RP-HPLC using a Zorbax C-18 column (4.6×250 mm), 60% to 92% MeOH in water over 45 min. The retention time is 36.15 min. MALDI-TOF MS (m/z) calculated for $C_{101}H_{144}N_{21}O_{21}P$ (M)+, 2018.06; found (M–H)−, 2017.21.

Synthesis of gA hydrolysis product (FIG. 16, structure 7): Gramicidamine (8 mg, 4.3 µmol) was dissolved in 1.5 mL of THF and DIEA (3.8 µL, 9.9 µmol) was added. O-trityl glycolic acid, (1.7 mg, 8.6 mmol) and EEDQ (2.1 mg, 8.6 µmol) were separately added to the solution. The reaction was stirred for 12 h. The trityl-protected derivative of gA hydrolysis product was purified by preparative silica chromatography with DCM:MeOH (9:1) and was dissolved in 1 mL of DCM and cooled to 0° C. A solution of 1 mL TFA/DCM (1:1) with 0.02 mL of dimethylsulfide and 0.01 mL of ethanedithiol is cooled to 0° C. The TFA solution is then added to the solution containing the trityl-protected derivative of gA hydrolysis product. The reaction was stirred at 23° C. for 4 h. Upon purification by silica chromatography with DCM/MeOH (9:1) as eluent, 6 mg (72% yield) of gA hydrolysis product was obtained. ESI-MS (m/z) calculated for $C_{101}H_{143}N_{21}O_{18}$ (M)+., 1939.35; found (M+Na) +, 1962.01.

Monitoring the enzymatic hydrolysis of glycolic acid-O-phosphate with Alkaline Phosphatase by NMR: Glycolic acid-O-phosphate (1.1 mg, 7.1 µmol) was added to a buffer containing 0.5 mL of 100 mM KCl, 140 mM $Na_2CO_3$ buffer in 0.5 mL of $D_2O$ at pD 9.4. Alkaline phosphate (0.5 mg, 1 nmol) was added to the solution and $^{31}$P-NMR spectra were taken at various time points to monitor the enzymatic hydrolysis of glycolic acid-O-phosphate to glycolic acid. $^{31}$P-NMR (300 MHz, $D_2O$): glycolic acid-O-phosphate: δ 3.33 ppm, free inorganic phosphate: 2.54 ppm using an internal 85% phosphoric acid standard (set to 0 ppm). The reaction was completed after 50 min.

The entirety of each patent, patent application, publication, document and sequence (e.g., nucleotide sequence, amino acid sequence) referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

It is to be understood that the disclosure is not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the invention(s), specific examples of appropriate materials and methods are described herein.

The examples set forth above are provided to give those of ordinary skill in the art a complete disclosure and description of how to make and use the embodiments of the devices, systems and methods of the disclosure, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. A method for detecting a target analyte in a biological sample, the method comprising:
   a) contacting a biosensor with a biological sample comprising a target analyte, wherein
      (i) the biosensor comprises a membrane; and
      (ii) the membrane comprises a first and a second layer each comprising closely packed amphiphilic molecules, and a plurality of ionophore conjugates comprising an ion channel forming peptide and a substrate associated with the peptide;
   b) allowing the target analyte to modify the charge of at least one of the substrates thereby increasing or decreasing the flow of ions associated with at least one of the ionophore conjugates; and
   c) detecting a change in the conductance of the at least one of the ionophore conjugates thereby detecting a target analyte in a biological sample, wherein a change in the charge of the substrate detectably alters the flow of ions associated with the ionophore.

2. The method according to claim 1, wherein the substrate is associated with the peptide at the entrance of a channel formed by the peptide.

3. The method according to claim 1, wherein the target analyte is an enzyme.

4. The method according to claim 3, wherein the enzyme is a phosphatase or a kinase.

5. The method according to claim 1, wherein the ion channel forming peptide is selected from the group consisting of gramicidin, band three protein, bacteriorhodopsin, proteorhodopsin, mellitin, alamethicin, an alamethicin analogue, porin, tyrocidine, tyrothricin, and valinomycin.

6. The method according to claim 5, wherein the gramicidin is gramicidin A, gramicidin B, gramicidin C, gramicidin D, gramicidin GT, gramicidin GM, gramicidin GM$^-$, gramicidin GN$^-$, and gramicidin A'.

7. The method according to claim 6, wherein the gramicidin is gramicidin A.

8. The method according to claim 1, wherein the substrate comprises a moiety suitable for phosphorylation.

9. The method according to claim 1, wherein the substrate comprises a moiety suitable for de-phosphorylation by a phosphatase.

10. The method according to claim 9, wherein the moiety is a negatively-charged phosphate group.

11. The method according to claim 10, wherein the phosphatase is alkaline phosphatase.

12. The method according to claim 1, wherein the substrate is glycolic-O-phosphate.

13. The method according to claim 1, wherein the ionophore conjugate further comprises a spacer group that covalently links the ionophore to the substrate moiety.

14. The method according to claim 13, wherein the spacer group is selected from the group consisting alkyl, alkyl amides, alkyl esters, alkyl carbamates, alkyl carbonates, oligomers of alkylidene glycol, combinations of oligomers of ethylene glycol with amides, esters or carbamates, and oligopeptides.

15. The method according to claim 1, wherein the target analyte is derived from a biological fluid.

16. The method according to claim 1, wherein the amphiphilic molecules are phospholipids.

17. The method according to claim 16, wherein the phospholipids are zwitterionic or charged differently than the ion channel forming peptide.

* * * * *

UNITED STATES PATENT AND TRADEMARK OFFICE
CERTIFICATE OF CORRECTION

| | | |
|---|---|---|
| PATENT NO. | : 8,586,369 B2 | Page 1 of 1 |
| APPLICATION NO. | : 12/668178 | |
| DATED | : November 19, 2013 | |
| INVENTOR(S) | : Jerry Yang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 704 days.

Signed and Sealed this
Eleventh Day of August, 2015

Michelle K. Lee
*Director of the United States Patent and Trademark Office*